(12) United States Patent
Ivosevic et al.

(10) Patent No.: US 11,491,280 B2
(45) Date of Patent: Nov. 8, 2022

(54) PLASTIC STOPPER

(71) Applicant: Becton, Dickinson and Company, Franklin Lakes, NJ (US)

(72) Inventors: Milan Ivosevic, Kinnelon, NJ (US); Girum Yemane Tekeste, Hackensack, NJ (US); Andrew Wong, East Hanover, NJ (US); Michael Vincent Quinn, East Hanover, NJ (US); Andrzej Baranski, Chatham, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 544 days.

(21) Appl. No.: 16/713,553

(22) Filed: Dec. 13, 2019

(65) Prior Publication Data

US 2020/0114085 A1    Apr. 16, 2020

Related U.S. Application Data

(63) Continuation of application No. 15/477,238, filed on Apr. 3, 2017, now Pat. No. 10,543,318, which is a
(Continued)

(51) Int. Cl.
*A61M 5/315*    (2006.01)
*A61M 5/31*    (2006.01)

(52) U.S. Cl.
CPC ...... *A61M 5/31513* (2013.01); *A61M 5/3129* (2013.01); *A61M 5/31515* (2013.01);
(Continued)

(58) Field of Classification Search
CPC ......... A61M 5/31513; A61M 5/31511; A61M 5/31515; A61M 5/315; A61M 2005/31508; A61M 2005/31521; A61M 2005/5073
See application file for complete search history.

(56) References Cited

U.S. PATENT DOCUMENTS 3,147,753 A    9/1964  Nogier et al.
3,176,595 A    4/1965  Schwartz
(Continued)

FOREIGN PATENT DOCUMENTS

DE    2720125 A1    11/1978
EP    0026940 A1    4/1981
(Continued)

*Primary Examiner* — Rebecca E Eisenberg
(74) *Attorney, Agent, or Firm* — The Webb Law Firm

(57) ABSTRACT

A stopper includes a main body portion defining an open rearward end configured to receive the plunger rod, an engagement portion provided along an inner circumference of the main body portion configured to engage at least a top portion of the plunger rod, a closed front end forming a flexible roof, and a first perimetrical skirt extending around an outer circumference of the main body portion toward the closed front end of the main body portion. When fluid pressure is increased inside the syringe barrel during an injection, the flexible roof expands in a radial direction toward an inner wall of the syringe barrel, the first perimetrical skirt is forced against the inner wall of the syringe barrel, and an engagement between the plunger rod and the engagement portion forces the main body portion to expand in the radial direction toward the inner wall of the syringe barrel.

18 Claims, 22 Drawing Sheets

Related U.S. Application Data continuation of application No. 13/432,647, filed on Mar. 28, 2012, now Pat. No. 9,642,969.

(60) Provisional application No. 61/468,304, filed on Mar. 28, 2011.

(52) U.S. Cl.
CPC ............. *A61M 2005/31516* (2013.01); *A61M 2005/31521* (2013.01)

(56) References Cited

U.S. PATENT DOCUMENTS

| | | | |
|---|---|---|---|
| D203,730 S | 2/1966 | Coanda | |
| 3,253,592 A | 5/1966 | Von Pechmann | |
| 3,354,882 A | 11/1967 | Coanda | |
| 4,057,052 A | 11/1977 | Kaufman et al. | |
| 4,215,701 A | 8/1980 | Raitto | |
| 4,266,557 A | 5/1981 | Merry | |
| 4,354,507 A | 10/1982 | Raitto | |
| 4,363,329 A | 12/1982 | Raitto | |
| 4,704,105 A | 11/1987 | Adorjan et al. | |
| 4,852,768 A | 8/1989 | Bartsch | |
| 4,969,884 A | 11/1990 | Yum | |
| 4,997,423 A | 3/1991 | Okuda et al. | |
| 5,009,646 A | 4/1991 | Sudo et al. | |
| 5,127,906 A | 7/1992 | Landry, Jr. et al. | |
| 5,181,912 A | 1/1993 | Hammett | |
| 5,275,582 A | 1/1994 | Wimmer | |
| 5,314,416 A | 5/1994 | Lewis et al. | |
| 5,395,345 A | 3/1995 | Gross | |
| 5,397,313 A | 3/1995 | Gross | |
| 5,496,285 A | 3/1996 | Schumacher et al. | |
| 5,620,423 A | 4/1997 | Eykmann et al. | |
| 5,735,825 A | 4/1998 | Stevens et al. | |
| 6,004,300 A | 12/1999 | Butcher et al. | |
| 6,053,895 A | 4/2000 | Kolberg et al. | |
| 6,142,977 A | 11/2000 | Kolberg et al. | |
| 6,213,985 B1 | 4/2001 | Niedospial, Jr. | |
| 6,224,577 B1 | 5/2001 | Dedola et al. | |
| 6,398,763 B1 | 6/2002 | Richardson et al. | |
| 6,432,089 B1 | 8/2002 | Kakimi et al. | |
| 6,562,009 B1 | 5/2003 | Schottli | |
| 6,626,870 B1 | 9/2003 | Yarborough et al. | |
| 6,942,638 B1 | 9/2005 | Quinn | |
| 7,070,581 B2 | 7/2006 | Manera et al. | |
| 7,195,609 B2 | 3/2007 | Huegli | |
| 7,438,552 B2 | 10/2008 | Manera et al. | |
| 7,621,888 B2 * | 11/2009 | Chen | A61M 5/322 604/110 |
| 7,727,202 B2 | 6/2010 | Kirchhofer et al. | |
| 2002/0022806 A1 | 2/2002 | Witowski | |
| 2005/0137533 A1 | 6/2005 | Sudo et al. | |
| 2006/0069356 A1 | 3/2006 | Witowski | |
| 2007/0219508 A1 | 9/2007 | Bisegna et al. | |
| 2007/0265574 A1 | 11/2007 | Tennican et al. | |
| 2008/0083789 A1 | 4/2008 | Brugner | |
| 2008/0300550 A1 | 12/2008 | Schiller et al. | |
| 2008/0300551 A1 * | 12/2008 | Schiller | A61M 5/31511 604/220 |
| 2009/0048560 A1 | 2/2009 | Caizza et al. | |
| 2009/0062749 A1 | 3/2009 | Manera et al. | |
| 2010/0016807 A1 * | 1/2010 | Thilly | A61M 5/31513 604/218 |
| 2010/0130935 A1 | 5/2010 | Hieb et al. | |

FOREIGN PATENT DOCUMENTS

| | | |
|---|---|---|
| FR | 1333235 A | 7/1963 |
| FR | 1500009 A | 11/1967 |
| FR | 1520582 A | 4/1968 |
| FR | 2641525 A1 | 7/1990 |
| JP | 08238316 A | 9/1996 |
| JP | 2002505161 A | 2/2002 |
| JP | 2002263187 A | 9/2002 |
| JP | 2003135487 A | 5/2003 |
| JP | 2003522608 A | 7/2003 |
| JP | 200424423 A | 1/2004 |
| JP | 2004121344 A | 4/2004 |
| JP | 2006500161 A | 1/2006 |
| JP | 2007268177 A | 10/2007 |
| JP | 2010528826 A | 8/2010 |
| WO | 8402278 A1 | 6/1984 |
| WO | 8500524 A1 | 2/1985 |
| WO | 8805315 A1 | 7/1988 |
| WO | 2006109272 A2 | 10/2006 |

\* cited by examiner

PLASTIC STOPPER

CROSS REFERENCE TO RELATED APPLICATIONS

This application is a continuation of U.S. patent application Ser. No. 15/477,238 entitled "Plastic Stopper", filed Apr. 3, 2017, which is a continuation of U.S. patent application Ser. No. 13/432,647 entitled "Plastic Stopper", filed Mar. 28, 2012 (now U.S. Pat. No. 9,642,969), which claims the benefit of U.S. Provisional Patent Application No. 61/468,304 entitled "Plastic Stopper" filed Mar. 28, 2011, each of which are hereby incorporated by reference in their entirety.

BACKGROUND OF THE INVENTION

Field of the Invention

The invention relates, in general, to a stopper assembly for use with a syringe and, more particularly, to a stopper assembly manufactured from a rigid or semi-rigid plastic material that provides an active sealing function.

Description of Related Art

Current syringe designs can typically be categorized as two-piece syringes or three-piece syringes. A typical three-piece syringe includes a tubular barrel having an access opening formed at one end, and a smaller discharge opening formed at the opposing end. The lead end of an elongated plunger is received within the access opening of the barrel so as to be slidable within the barrel. Attached to the lead end of the plunger is a flexible sealing member or stopper that snugly seals against the interior surface of the barrel. A needle, a threaded member, or a non-threaded member is usually attached to the discharge opening on the barrel. The needle can be used to penetrate a surface while the threaded member can be used to attach the syringe to another medical device, such as a catheter. The flexible stopper is usually manufactured from an elastomeric material, such as a rubber or a cross-linked or thermoplastic elastomer.

A two-piece syringe, on the other hand, includes a "stopper" that is in the form of a rigid sealing disc, also known as a plunger rod head. It is typically made of the same rigid plastic as the rest of plunger rod. The sealing force in a two-piece syringe comes from a thin elastic barrel that deforms around the rigid plunger rod head.

During use, the discharge end of the syringe is initially placed in contact with a fluid. For example, the needle on the syringe can be inserted into a liquid medication. As the plunger is retracted within the barrel, a process known as aspiration, a negative pressure is formed within the end of the barrel so as to cause the fluid to be drawn into the barrel. The syringe can then be moved to a second location where advancing the plunger within the barrel causes the fluid to be pushed or expressed out the discharge end of the barrel.

Current two-piece and three-piece syringe designs suffer from various deficiencies. For instance, three-piece syringes that include an elastomeric or rubber stopper have a high passive contact pressure between the stopper and syringe barrel that is present during the shelf life and when the syringe is in use. This passive contact pressure can be as high as approximately 300 psi or more. Accordingly, the syringe barrel requires relatively large barrel wall thickness in order to prevent localized barrel creep or bulging during the shelf life. Therefore, a need exists for a syringe that has a lower contact pressure between the stopper and the barrel such that localized bulging of the syringe barrel is eliminated. Typical two-piece syringes also include such high passive contact pressures and suffer from similar deficiencies. Therefore, a need exists for a syringe manufactured using less material to achieve thinner walls by addressing the bulging effect caused by current stopper designs.

In addition, due to the high contact forces and high friction coefficient between current elastomeric or rubber stoppers and the inner wall of the barrels, current syringe designs must be lubricated with a liquid lubricant, such as silicone oil, so that break-loose and break-out hand forces required to operate the syringe are not too high. Accordingly, a need further exists for a plastic stopper that can be used with a syringe without silicone oil or other lubricants or that allows for significantly lower hand forces when used with a lubricant.

Furthermore, current rubber stoppers are typically manufactured from a specialized cross-linked rubber (e.g., polyisoprene) that requires a specialized compression molding/curing process. Such a process can significantly increase the cost of manufacturing the syringe. Furthermore, significant waste materials are also produced during the compression molding process. For example, in a typical manufacturing process, up to 30% of the rubber is discarded during manufacturing of the conventional elastomeric stopper. Accordingly, a need exists for a stopper that can be efficiently manufactured, thereby reducing the cost of manufacturing the syringe and reducing the waste materials produced during the manufacturing of the syringe.

Conventional two-piece syringes also suffer from a variety of deficiencies. More particularly, conventional two-piece syringes typically include rigid plunger rod sealing edges. Such edges create very high contact forces which increase the hand force necessary to move the plunger. In addition, these high contact forces along the sealing edges significantly deform the barrel walls, which make two-piece syringes incompatible with syringe pumps where the barrel bulge can interfere with a pump clamping mechanism. Accordingly, a need exists for a syringe that has a lower contact pressure between the stopper and the barrel such that localized bulging of the syringe barrel is eliminated.

SUMMARY OF THE INVENTION

It is an object of the invention to provide a rigid plastic stopper that allows for thinner syringe barrel walls relative to the rubber-based conventional syringe stoppers. This is achieved because contact pressure between the rigid plastic stopper and the syringe barrel manufactured from a similar material is much lower when the syringe is not in use relative to a conventional rubber stopper. This allows for the elimination of barrel creep or localized bulging issues. In addition, the thinner barrel wall provided by the lower contact pressure in the syringe of the present invention also allows for lower material use and lower waste generation, thereby providing a "greener" syringe.

Furthermore, the lower contact pressure is achieved by providing the inventive rigid plastic stopper with an active sealing function such that when fluid pressure inside the syringe increases due to injection, sealing pressure between the stopper and the barrel also increases due to three separate pressure activated actions. The first of these actions is a flexing roof action in which a flexible roof of the stopper flexes inward and expands sideways in a radial direction. The next action is a flexing skirt action in which a perimetrical skirt extending around a main body portion of the stopper bends toward a wall of the syringe barrel. Finally, a sliding action is provided in which an engagement between the plunger rod and a notch formed in an interior portion of the main body portion of the stopper forces the main body portion to expand in the radial direction toward the inner wall of the syringe barrel. In addition, the present invention contemplates any of these three separate pressure activated actions, either individually or in combination, to be incorporated into a stopper.

A further object of the invention is to provide a plastic stopper that can be used with a syringe without silicone oil or other lubricants or that allows for significantly lower hand forces when used with a lubricant. The plastic stopper of the present invention is able to achieve these features due to a significantly lower coefficient of friction and contact area/pressure relative to a conventional rubber stopper. Another object of the invention is to provide a plastic stopper that is manufactured of the same or similar resins for other injection molded syringe parts. This allows for a reduction in the cost relating to material logistics and supply. Additionally, the plastic stopper of the invention is manufactured using significantly less material by weight relative to the conventional elastomers. The lower material use can translate to lower cost and lower waste generation.

The particularly disclosed stopper design is manufactured from a rigid plastic material while also providing an active sealing function. The stopper is adapted for attachment with a plunger rod for use within a syringe barrel.

According to one aspect of the invention, the stopper includes a main body portion defining an open rearward end configured to receive the plunger rod, an engagement portion provided along an inner circumference of the main body portion configured to engage at least a top portion of the plunger rod, a closed front end forming a flexible roof, and a first perimetrical skirt extending around an outer circumference of the main body portion toward the closed front end of the main body portion. When fluid pressure is increased inside the syringe barrel during an injection, the flexible roof expands in a radial direction toward an inner wall of the syringe barrel, the first perimetrical skirt is forced against the inner wall of the syringe barrel, and an engagement between the plunger rod and the engagement portion forces the main body portion to expand in the radial direction toward the inner wall of the syringe barrel, thereby providing a sealing pressure between the stopper and the inner wall of the syringe barrel. The stopper may further include a second perimetrical skirt extending around an outer circumference of the main body portion toward the open rearward end of the main body such that the second perimetrical skirt provides stability to the stopper in an axial direction. When fluid pressure is decreased inside the syringe barrel during an aspiration, the second perimetrical skirt is forced against the inner wall of the syringe barrel, thereby providing a sealing pressure between the stopper and the inner wall of the syringe barrel.

The closed front end of the main body may have a conical shape with a tip. The tip may include an extended portion configured to fit inside a tip of the syringe barrel. In addition, an extension extending from the tip toward the open rearward end may be provided in connection with the plunger rod to cause the flexible roof to expand in the radial direction toward the inner wall of the syringe barrel during an aspiration.

The engagement portion may be configured as a notch and the top portion of the plunger rod may include a tapered ring that engages the notch of the main body such that the engagement between the plunger rod and the notch forces the main body portion to expand in the radial direction toward the inner wall of the syringe barrel during both an injection and an aspiration. The notch may include an upwardly angled portion and a downwardly angled portion. The upwardly angled portion may have an angle of about 10° to about 80° as measured from a horizontal line extending between the upwardly angled portion and the downwardly angled portion, and desirably an angle of about 25° to about 55° as measured from a horizontal line extending between the upwardly angled portion and the downwardly angled portion. The downwardly angled portion may have an angle of about 10° to about 80° as measured from a horizontal line extending between the upwardly angled portion and the downwardly angled portion, and desirably an angle of about 25° to about 55° as measured from a horizontal line extending between the upwardly angled portion and the downwardly angled portion. Alternatively, the engagement portion may include a protruding portion and the top portion of the plunger rod may include a notch formed around an outer circumference thereof that engages the protruding portion of the main body such that the engagement between the plunger rod and the protruding portion forces the main body portion to expand in the radial direction toward the inner wall of the syringe barrel during both an injection and an aspiration.

The stopper, the plunger rod, and the syringe barrel may all be manufactured from the same rigid or semi-rigid polymeric material. The rigid or semi-rigid polymeric material may have an elastic modulus in the range of about 0.01 GPa to about 5 GPa, and desirably in the range of about 0.6 GPa to about 2 GPa. The rigid or semi-rigid polymeric material may be selected from the group consisting of: polyolefines, polyamides, polyesters, polystyrene, polyurethane, polycarbonate, acrylonitrile-butadiene-styrene, fluoropolymers, ionomers, polyacrylates, or any combination thereof.

The flexible roof may have a thickness of about 0.1 mm to about 3 mm, and desirably a thickness about 0.3 mm to about 1.2 mm. The first perimetrical skirt may have a thickness of about 0.05 mm to about 3 mm, and desirably a thickness of about 0.2 mm to about 0.5 mm. The length of the first perimetrical skirt may be about 1 mm to about 10 mm. The second perimetrical skirt may have a thickness of about 0.05 mm to about 3 mm, and desirably a thickness of about 0.2 mm to about 0.5 mm. The length of the second perimetrical skirt may be about 1 mm to about 10 mm.

According to another aspect of the invention, a syringe includes a substantially cylindrical syringe barrel having a fluid dispensing end and an open end; a stopper configured to be received within the open end of the syringe barrel; and a plunger rod having a plunger rod body extending along a longitudinal axis. The stopper includes a main body portion defining an open rearward end configured to receive the plunger rod, an engagement portion provided along an inner circumference of the main body portion, a closed front end forming a flexible roof, and a first perimetrical skirt extending around an outer circumference of the main body portion toward the closed front end of the main body. The plunger rod body includes a front attachment end configured to engage the engagement portion provided along the inner circumference of the main body portion of the stopper and a back end. When fluid pressure is increased inside the syringe barrel during an injection, the flexible roof expands in a radial direction toward an inner wall of the syringe barrel, the first perimetrical skirt is forced against the inner wall of the syringe barrel, and an engagement between the plunger rod and the engagement portion forces the main body portion to expand in the radial direction toward the inner wall of the syringe barrel, thereby providing a sealing pressure between the stopper and the inner wall of the syringe barrel.

The front attachment end of the syringe plunger body may include an extension portion configured to contact a lower surface of the flexible roof during an injection, thereby limiting the expansion of the flexible roof in the radial direction.

According to yet another aspect of the invention, a plunger rod and stopper assembly adapted for use with a syringe barrel includes a stopper and a plunger rod having a plunger rod body extending along a longitudinal axis. The stopper includes a main body portion defining an open rearward end configured to receive the plunger rod, an engagement portion provided along an inner circumference of the main body portion, a closed front end forming a flexible roof, and a first perimetrical skirt extending around an outer circumference of the main body portion toward the closed front end of the main body. The plunger rod includes a front attachment end configured to engage the engagement portion provided along the inner circumference of the main body portion of the stopper and a back end. When fluid pressure is increased inside the syringe barrel during an injection, the flexible roof expands in a radial direction toward an inner wall of the syringe barrel, the first perimetrical skirt is forced against the inner wall of the syringe barrel, and an engagement between the plunger rod and the engagement portion forces the main body portion to expand in the radial direction toward the inner wall of the syringe barrel, thereby providing a sealing pressure between the stopper and the inner wall of the syringe barrel.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

DETAILED DESCRIPTION OF THE INVENTION

Figure 1:
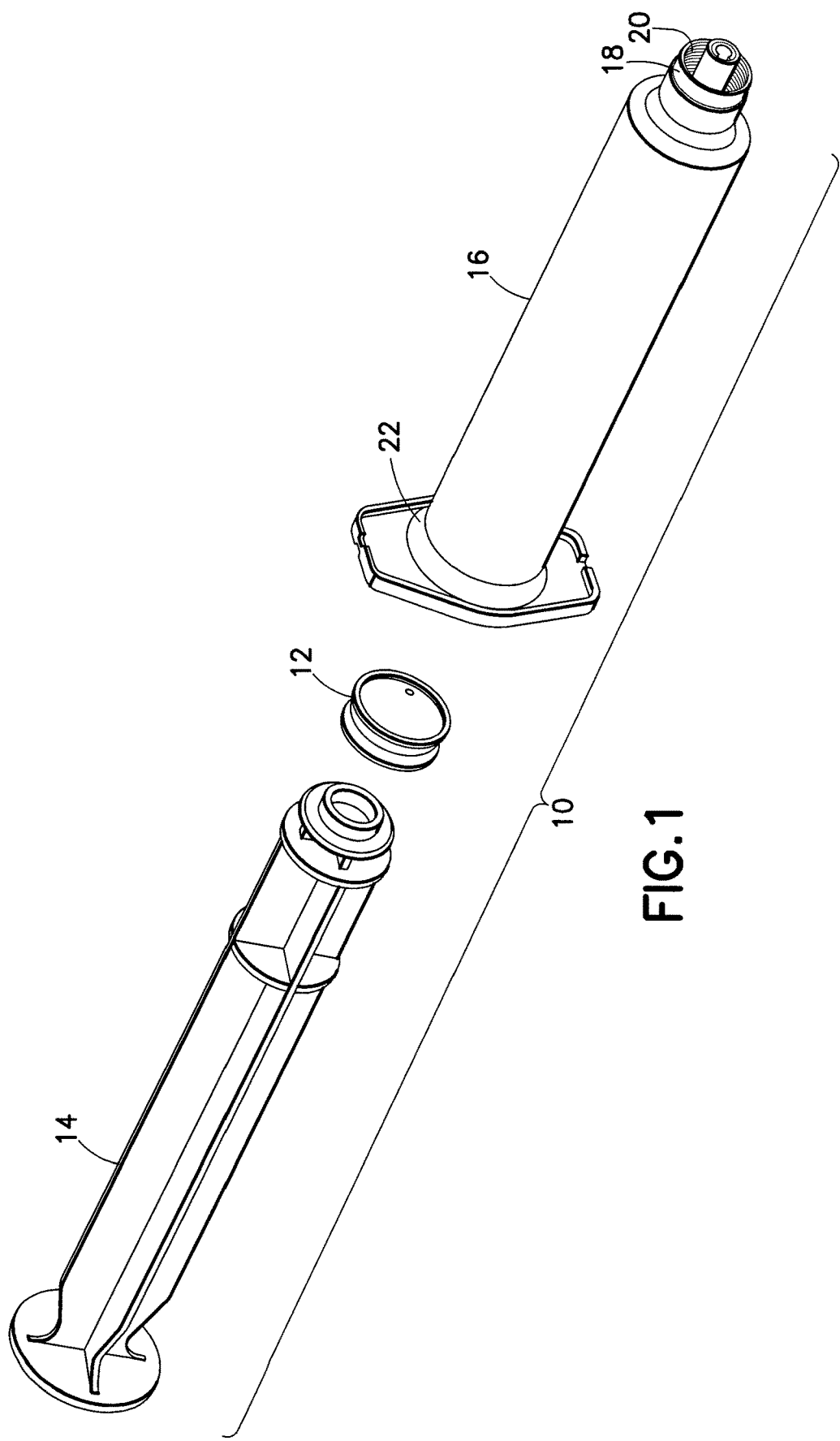
FIG. 1 is an exploded perspective view of a plunger rod, stopper, and syringe barrel in accordance with an embodiment of the present invention.

For purposes of the description hereinafter, the terms "upper", "lower", "right", "left", "vertical", "horizontal", "top", "bottom", "lateral", "longitudinal", and derivatives thereof, shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

With reference to FIG. 1, a syringe, generally denoted as reference numeral 10, includes a stopper 12 and a plunger rod 14. The stopper 12 and plunger rod 14 are adapted for use within a syringe barrel 16. The syringe barrel 16 includes a distal or frontal end 18 which includes an outlet opening and/or a mechanism for attachment of a separate medical device (such as a catheter), shown in the form of a luer 20, and an open proximal or rearward end 22 for receiving the stopper 12 and plunger rod 14 assembly. However, while the use of a luer type attachment is illustrated in FIG. 1, this is not to be construed as limiting the present invention as any suitable type of attachment for syringe 10 has been contemplated. In addition, in certain syringe pump applications where a low constant flow rate is required, an inner diameter of the syringe type should have a maximum value of about 1.30 mm. The purpose of this small inner diameter is to increase pressure during a low flow rate infusion therapy. The increased pressure inside the syringe forces the flexible roof, described hereinafter, to expand in a radial direction toward an inner wall of the syringe barrel and form a seal. For equal and constant flow rate, the small 1.30 mm syringe tip inner diameter requires or creates a higher pressure than a standard syringe tip inner diameter. While the figures herein depict a separate stopper and plunger assembly, it is contemplated that the stopper features may be integrally formed with the plunger rod 14.

Figure 2:
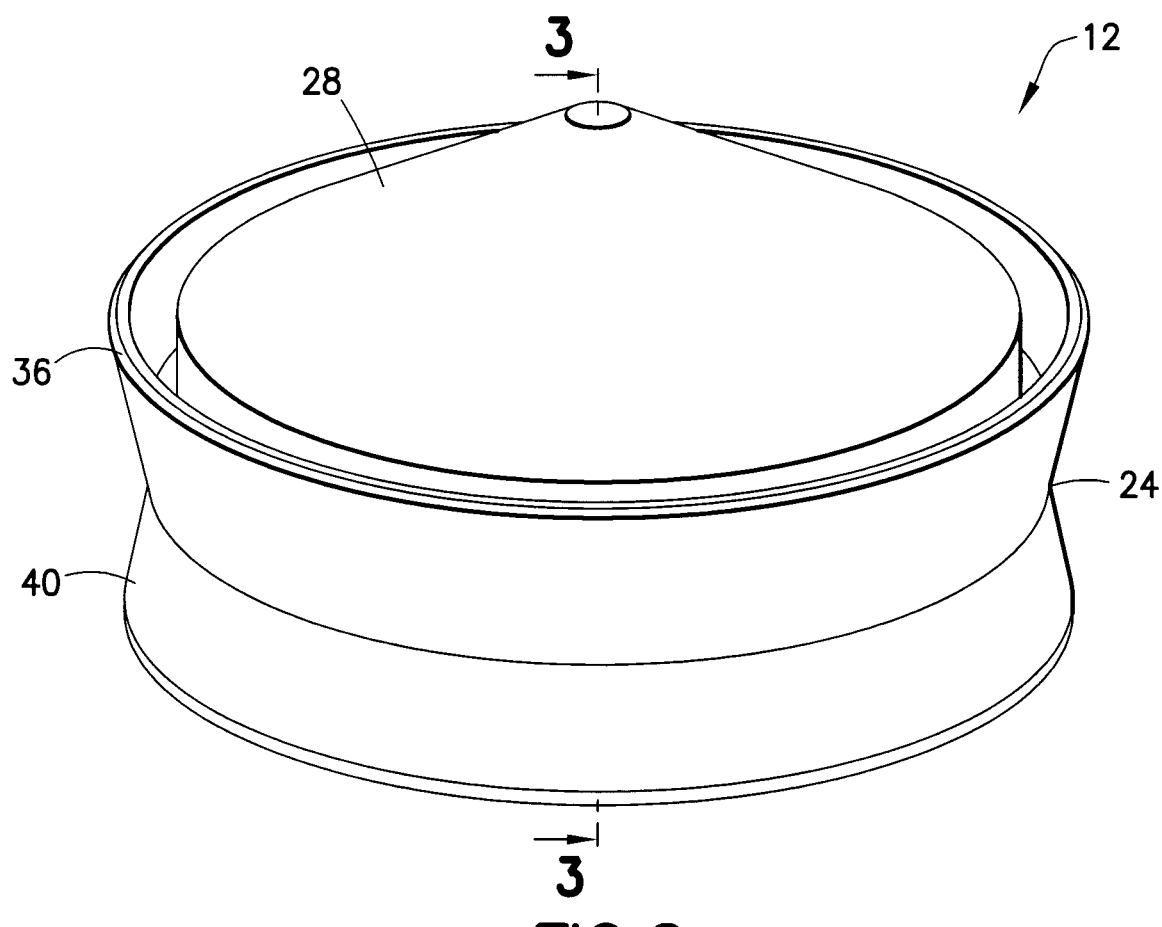
FIG. 2 is a perspective view of a stopper according to a first embodiment of the present invention.
Figure 3:
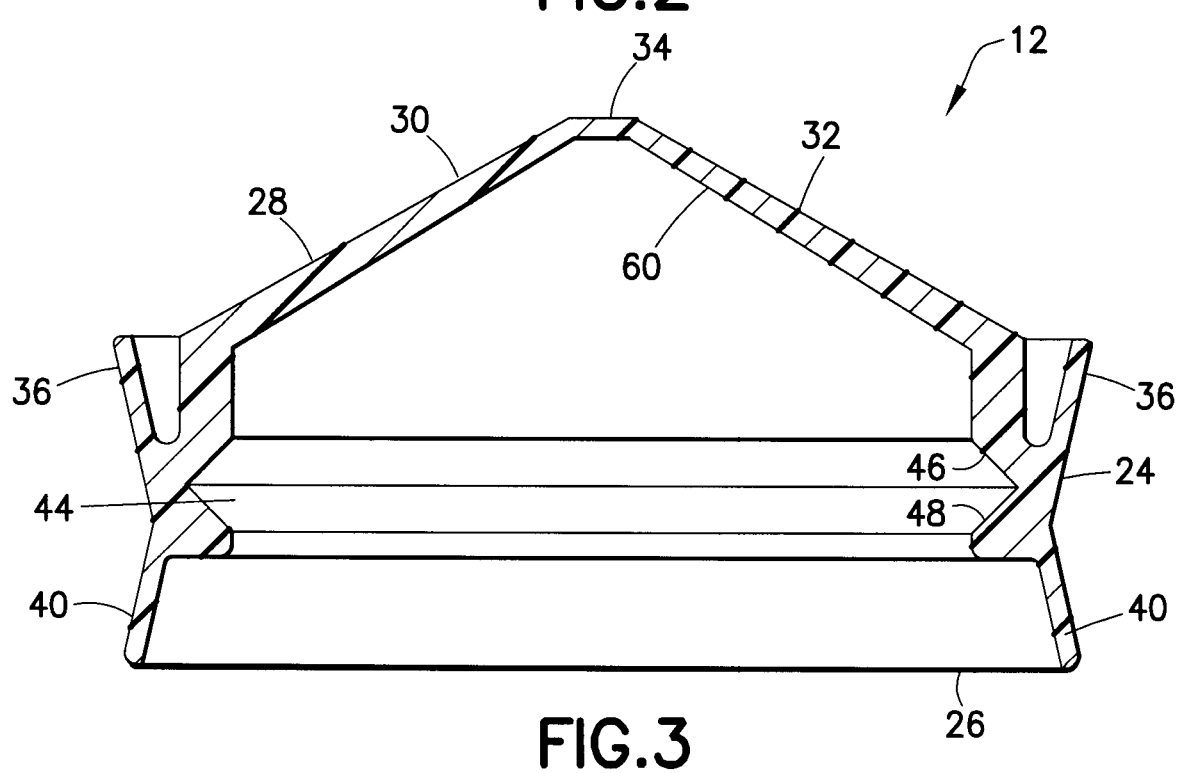
FIG. 3 is a cross-sectional side view of the stopper of FIG. 2 taken along line 3-3.

With reference to FIGS. 2 and 3, a first embodiment of the stopper 12 includes a main body portion 24 defining an open rearward end 26 configured to receive the plunger rod 14 and a closed front end 28 that forms a flexible roof. The flexible roof has a thickness of about 0.1 mm to about 3 mm, and desirably a thickness of about 0.3 mm to about 1.2 mm. The closed front end 28 of the main body portion 24 includes a first angled portion 30 and a second angled portion 32, which are both part of a single conical surface, that extend toward a tip 34, thereby providing the closed front end 28 with a substantially conical appearance. However, this shape of the flexible roof is not to be considered as limiting the present invention as the roof may be flat. Such a roof would not provide flexing roof action in which a flexible roof of the stopper flexes inward and expands sideways in a radial direction. However, a stopper with a flat roof has been envisioned that includes a flexing skirt action in which a perimetrical skirt extending around a main body portion of the stopper bends toward a wall of the syringe barrel, and a sliding action that is provided in which an engagement between the plunger rod and a notch formed in an interior portion of the main body portion of the plunger forces the main body portion to expand in the radial direction toward the inner wall of the syringe barrel.

A first perimetrical skirt 36 is provided that extends around an outer circumference of the main body portion 24 toward the closed front end 28. The primary purpose of the first perimetrical skirt 36 is to provide an "active seal" between the stopper body and an inner wall 38 of the syringe barrel 16 as will be discussed in greater detail hereinafter. The first perimetrical skirt 36 has a thickness from about 0.05 mm to about 3 mm, and desirably a thickness of about 0.2 mm to about 0.5 mm. The length of the first perimetrical skirt 36 may be about 1 mm to about 10 mm. In addition, the first perimetrical skirt 36 includes a tip that comes in contact with the inner diameter of the syringe barrel 16. The tip may have any variety of localized shapes, such as, but not limited to, round, angled, serrated, etc.

The first perimetrical skirt 36 may create a "dead space" of unused medication or other fluid at the end of an injection. To minimize this "dead space", a protrusion (not shown) having a shape corresponding to the "dead space" may be added to the inside of the barrel roof of the syringe barrel 16. The protrusion is sized to correspond to the gap formed between the inside edge of the first perimetrical skirt 36 and the main body portion 24. In addition, the protrusion may incorporate an interruption or a plurality of interruptions.

The stopper 12 also includes a second perimetrical skirt 40 extending around an outer circumference of the main body portion 24 toward the open rearward end 26. The primary purpose of the second perimetrical skirt 40 is to provide stability to the stopper 12 in an axial direction and to prevent tilting of the stopper 12. In addition, when fluid pressure is decreased inside the syringe barrel 16 during an aspiration, the second perimetrical skirt 40 is forced against the inner wall 38 of the syringe barrel 16, thereby providing a sealing pressure between the stopper 12 and the inner wall 38 of the syringe barrel 16. The second perimetrical skirt 40 has a thickness from about 0.05 mm to about 3 mm, and desirably a thickness of about 0.2 mm to about 0.5 mm. The length of the second perimetrical skirt 40 may be about 1 mm to about 10 mm.

As shown in FIG. 3, the main body portion 24 of the stopper 12 is substantially hollow and designed to receive an attachment portion 42 of plunger rod 14. The main body portion 24 has a height, as measured from the bottom of the second perimetrical skirt 40 to the top of the first perimetrical skirt 36 of about 2 mm to about 20 mm, and desirably about 3 mm to about 8 mm. A notch 44 is provided that extends around an inner circumference of the main body portion 24. The notch 44 includes an upwardly angled portion 46 and a downwardly angled portion 48, thereby providing the notch 44 with a conical cross-sectional shape. The upwardly angled portion 46 has an angle of about 10° to about 80° as measured from a horizontal line, and desirably has an angle of about 25° to 55°. The downwardly angled portion 48 has an angle of about 10° to about 80° as measured from a horizontal line, and desirably has an angle of about 25° to 55°. However, the shape of notch 44 is not to be construed as limiting the present invention as other interfaces between the notch 44 and the attachment portion 42 of the plunger rod 14, such as linear or curved interfaces, could be utilized to provide the same function. In addition, with reference to FIG. 4B, a notch 64 may be provided at the end of the plunger rod 14 and the stopper 12 could include a protruding portion 66 that engages the notch 64, thereby providing the same function as the notch 44. While the shape of the notch 64 is shown in the figures as having a substantially conical cross-section, this shape is not to be construed as limiting the present invention as any suitable shape may be utilized.

The notch 44 is configured to engage with the attachment portion 42 of the plunger rod 14 such that, during an injection, the upwardly angled portion 46 engages the attachment portion 42, thereby forcing the main body portion 24 in a radial direction (i.e., toward barrel wall) such that a stronger seal is created between the main body portion 24 and the inner wall 38. During an aspiration, the downwardly angled portion 48 engages the attachment portion 42, thereby forcing the main body portion 24 in a radial direction (i.e., toward barrel wall) such that a stronger seal is created between the main body portion 24 and the inner wall 38.

The stopper 12 is desirably manufactured from a "rigid" or "semi-rigid" polymeric material with an elastic modulus in the range of about 0.01 to about 5 GPa, and desirably in the range of about 0.6 to about 2 GPa. The desired Shore D hardness of the material is between about D30 and about D80. The stopper material may include, but is not limited to polyolefines (e.g., PE, PP, and their copolymers), polyamides (e.g., nylons), polyesters (e.g., PET), polystyrene, polyurethane, polycarbonate, acrylonitrile-butadiene-styrene, fluoropolymers, ionomers, polyacrylates, or any other similar material. Moreover, any bio-derived, biodegradable, and recycled polymer with the elastic modulus between about 0.01 and about 5 GPa may also be used with the stopper in accordance with the present invention. Since the stopper 12 is manufactured from a "rigid" or "semi-rigid" polymeric material, a significantly lower coefficient of friction and contact area/pressure relative to a conventional rubber stopper is provided. Accordingly, the stopper 12 can be used with a syringe 10 without silicone oil or other lubricants. In addition, the syringe barrel 16 may be made of the same material or a similar material as the stopper 12.

Figure 5:
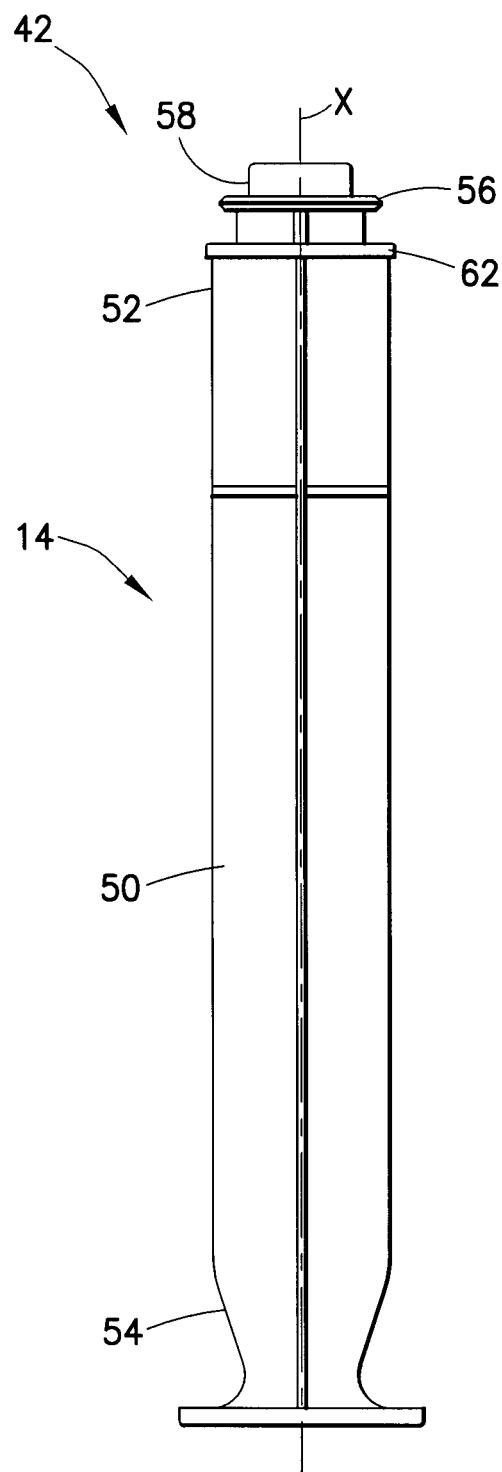
FIG. 5 is a side view of the plunger rod of FIG. 1.
Figure 6A:
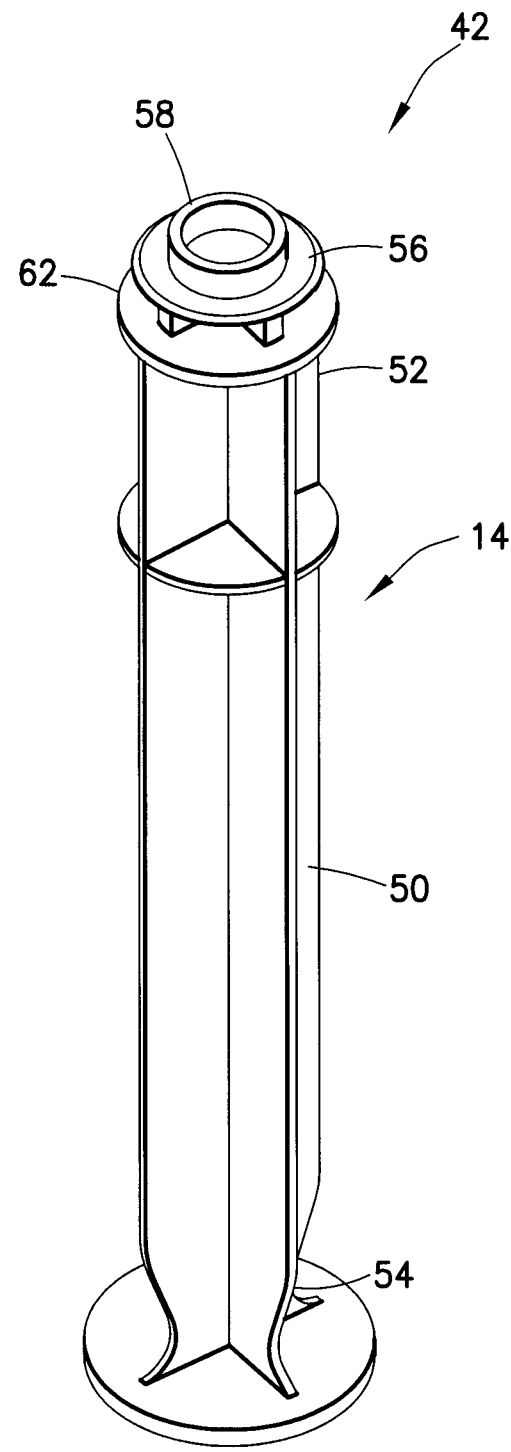
FIG. 6A is a perspective view of the plunger rod of FIG. 1.
Figure 6B:
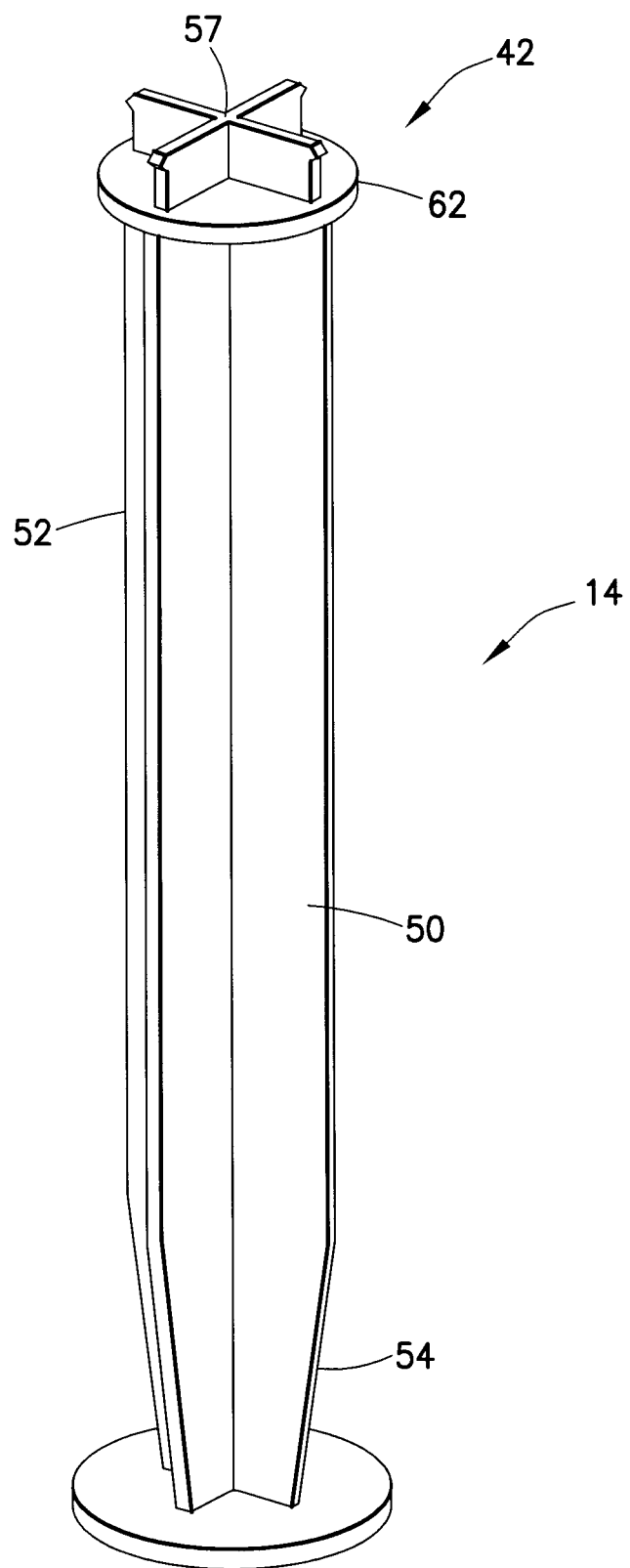
FIG. 6B is an alternative embodiment of the plunger rod of FIG. 6A.

With reference to FIGS. 5 and 6A, the plunger rod 14 may include a syringe plunger body 50 having a front end 52 and a back end 54 extending along a longitudinal axis X. The attachment portion 42 is associated with the front end 52 of the syringe plunger body 50. The attachment portion 42 includes a tapered ring 56 designed to engage the notch 44 of the stopper 12. Alternatively, a pair of discrete ribs 57 may be provided in place of tapered ring 56 (see FIG. 6B). The discrete ribs 57 may be arranged in a cross-shape as shown in FIG. 6B such that the ends of the ribs engage the notch 44 at four discrete points therealong. However, this configuration is not to be construed as limiting the present invention as any suitable number of discrete ribs may be utilized or an interrupted tapered ring may also be used. In addition, instead of a continuous notch that extends around an inner circumference of the main stopper body, a plurality of discrete notches, corresponding to the number of discrete ribs, may also be utilized.

Figure 4A:
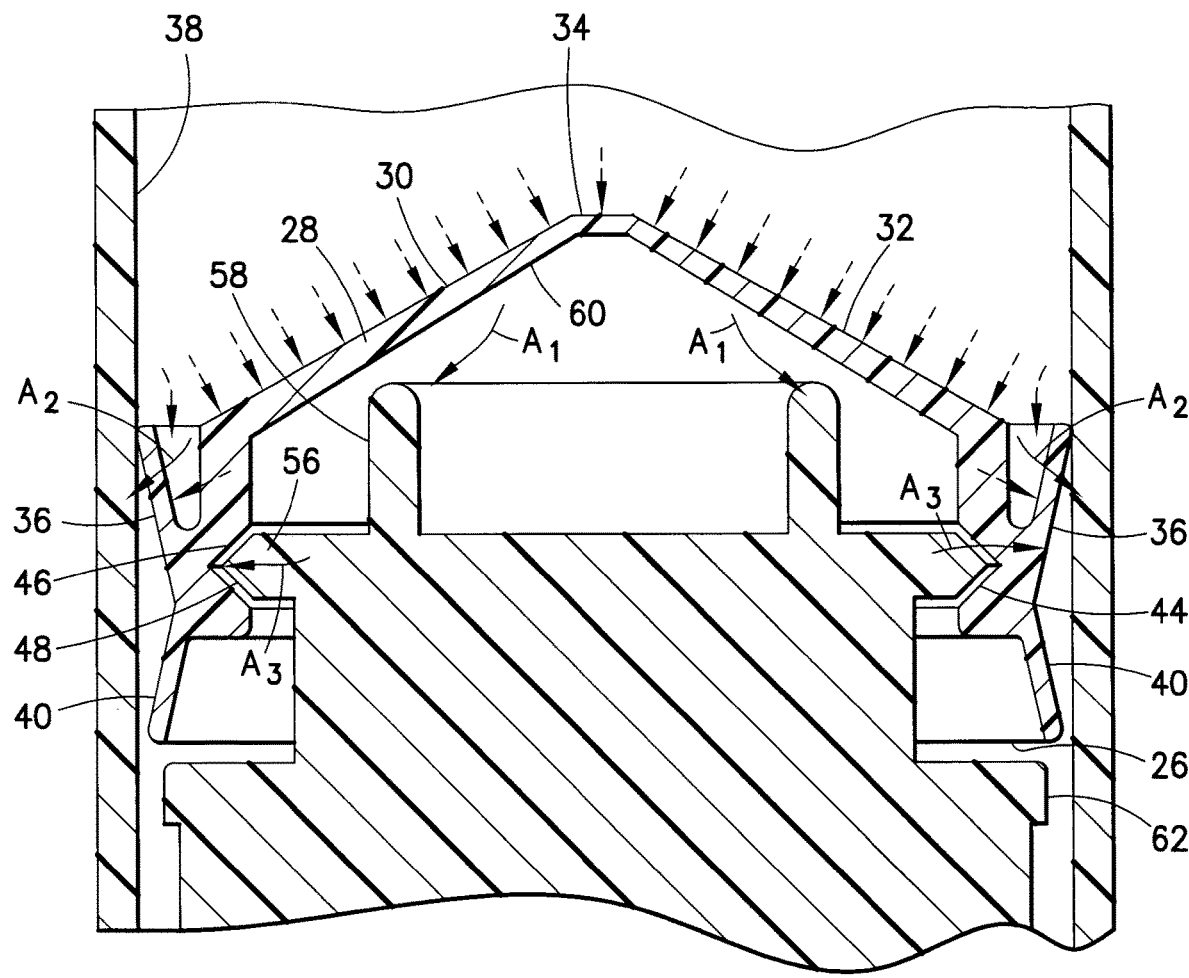
FIG. 4A is a cross-sectional side view of the stopper of FIG. 2 attached to a plunger rod and positioned within a syringe barrel.
Figure 4B:
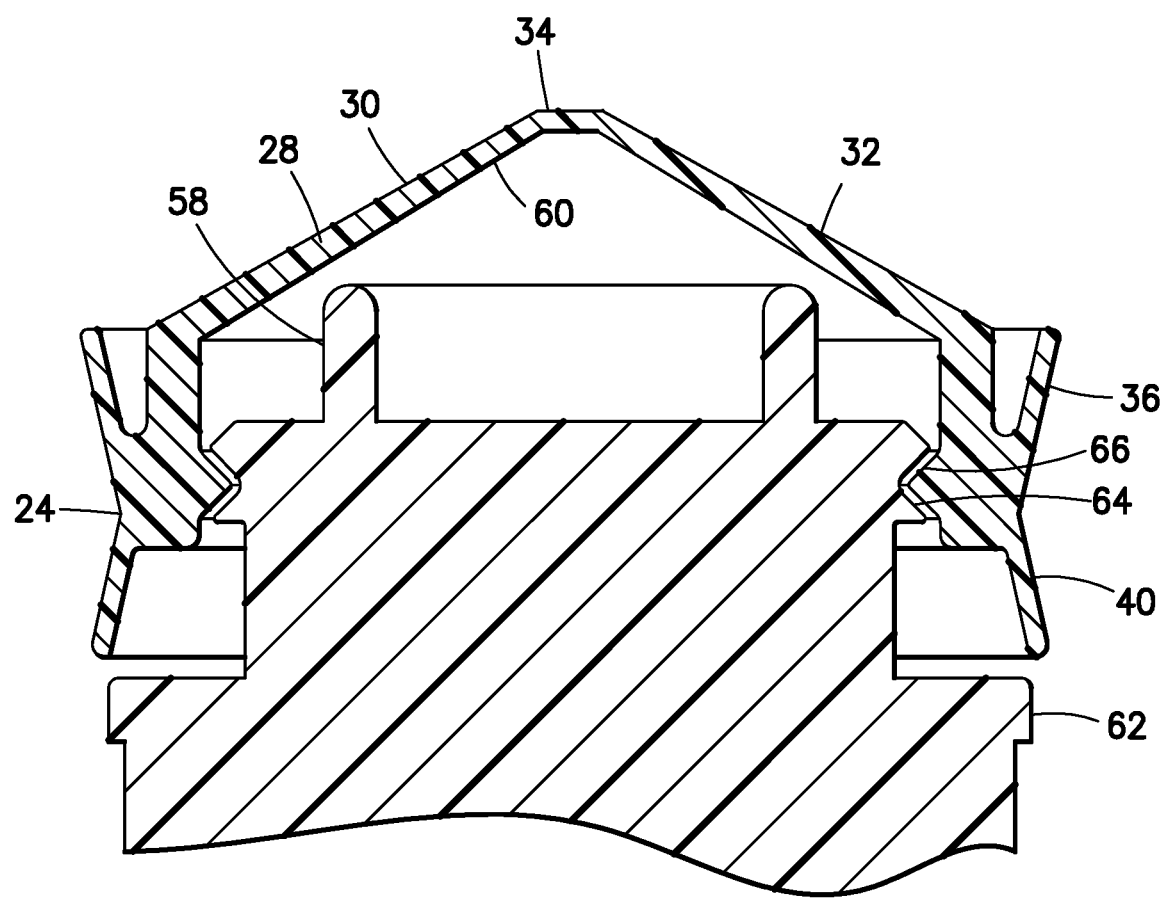
FIG. 4B is a cross-sectional side view of an alternative embodiment of the stopper of FIG. 2 having an alternative engagement mechanism between the stopper and the plunger rod.

The front end 52 of the plunger rod 14 may also include an extension portion 58 configured to contact a lower surface 60 of the flexible roof of the closed front end 28 during an injection only when or if maximum pressure reaches maximum design pressure, thereby limiting the expansion of the flexible roof in the radial direction to prevent the flexible roof from collapsing if the syringe 10 is over-pressurized in an extreme case. The syringe plunger body 50 may also include a retaining ring 62 positioned adjacent to the open rearward end 26 of the main body portion 24 of the stopper 12. The retaining ring 62 is provided to prevent the plunger rod 14 from being removed from the syringe barrel 16. With reference to FIG. 4A, when the plunger rod 14 is inserted into the stopper 12 through the open rearward end 26, the tapered ring 56 engages the notch 44 such that the plunger rod 14 is locked in place and is prevented from separating from the stopper 12.

The plunger rod 14 may be manufactured from the same material as the stopper 12. In addition, the plunger rod 14 and the stopper 12 may be manufactured integrally to provide a two-piece syringe or separately to provide a three-piece syringe.

Figure 7:
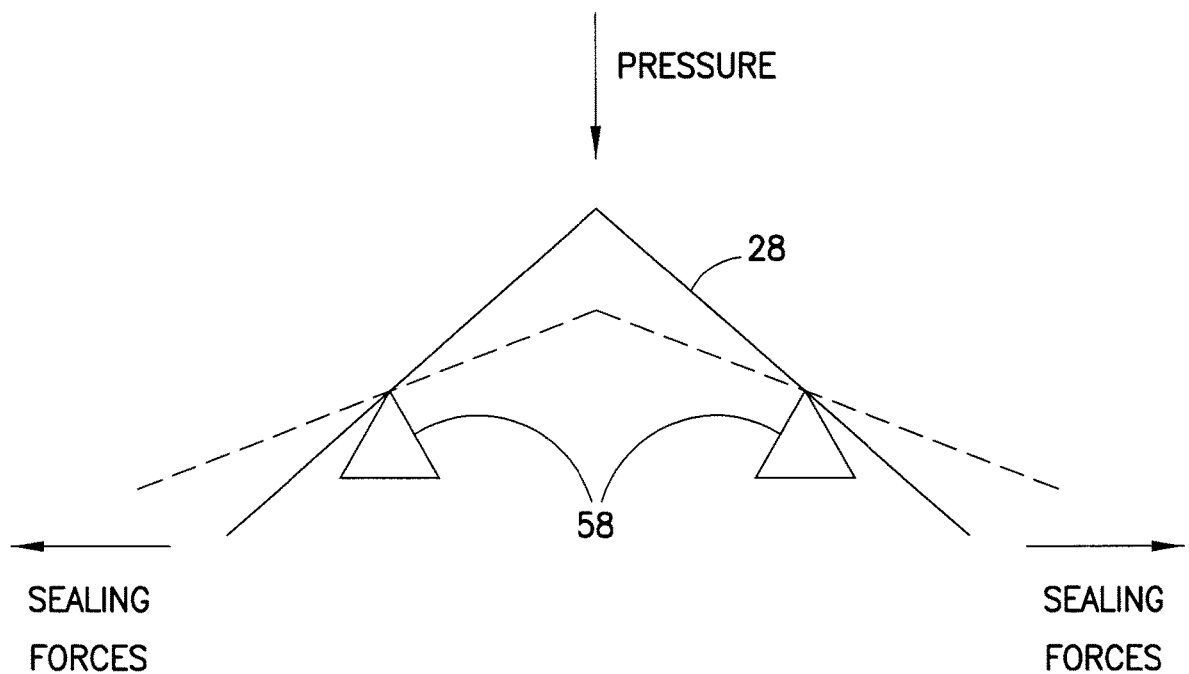
FIG. 7 is a schematic view of the flexible roof of the stopper of FIG. 2 in accordance with the present invention.

With continued reference to FIG. 4A, the rigid plastic stopper 12 includes an active sealing function such that when fluid pressure inside the syringe 10 increases due to injection, as shown by the dashed arrows, sealing pressure between the stopper 12 and the syringe barrel 16 also increases due to three separate pressure activated actions. The first of these actions is a flexing roof action in which the flexible roof of the closed front end 30 of the stopper 12 flexes inward and expands sideways in a radial direction as shown by arrows $A_1$. This action is further illustrated schematically in FIG. 7. As can be seen in FIG. 7, the flexible roof of the closed front end 30 of the stopper 12 is shown as a solid line before the pressure within the syringe barrel 16 is increased due to an injection. Once an injection is started, the pressure increase within the barrel causes the flexible roof of the closed front end 30 of the stopper 12 to flex inwardly and expand sideways in a radial direction as shown by the dashed line. The extension portions 58 limit this flexing such that the flexible roof does not invert during an injection.

A second action can be considered a flexing skirt action in which the first perimetrical skirt 36 extending around the main body portion 24 of the stopper 12 bends toward the inner wall 38 of the syringe barrel 16 as shown by arrows $A_2$.

Finally, a sliding action is provided in which the engagement between the tapered ring 56 of the plunger rod 14 and the notch 44 of the main body portion 24 of the stopper 12 forces the main body portion 24 to expand in the radial direction toward the inner wall 38 of the syringe barrel 16 as shown by arrows $A_3$. More specifically, the engagement between the upwardly angled portion 46 of the notch 44 and an upper edge of the tapered ring 56 ensures that the stopper 12 is forced in a radial direction (i.e., toward the inner wall 38) during an injection, thereby contributing to a stronger sealing between the stopper 12 and the syringe barrel 16. In addition, the engagement between the downwardly angled portion 48 of the notch 44 and a lower edge of the tapered ring 56 ensures that the stopper 12 is forced in a radial direction (i.e., toward the inner wall 38) during an aspiration, thereby contributing to a stronger sealing between the stopper 12 and the syringe barrel 16.

These active sealing functions allow for low contact pressure between the stopper 12 and the inner walls 38 of the syringe barrel 16, thereby eliminating barrel creep and localized bulging issues when the walls of the syringe barrel 16 are thin. The interface between the stopper 12 and the inner walls 38 of the syringe barrel 16 at assembly is between about 0.01 mm/per diameter and 2 mm/per diameter, and desirably, about 0.3 mm/per diameter and 0.8 mm/per diameter.

Figure 8:
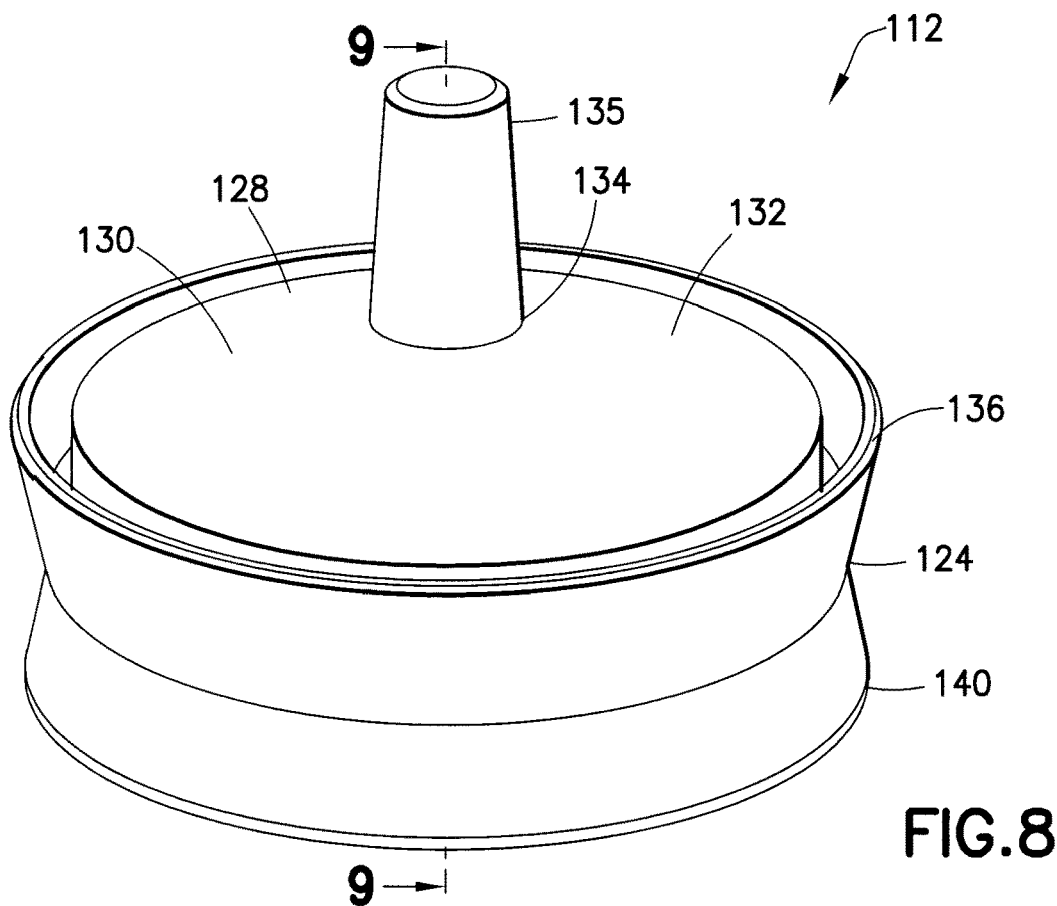
FIG. 8 is a perspective view of a stopper according to a second embodiment of the present invention.
Figure 9:
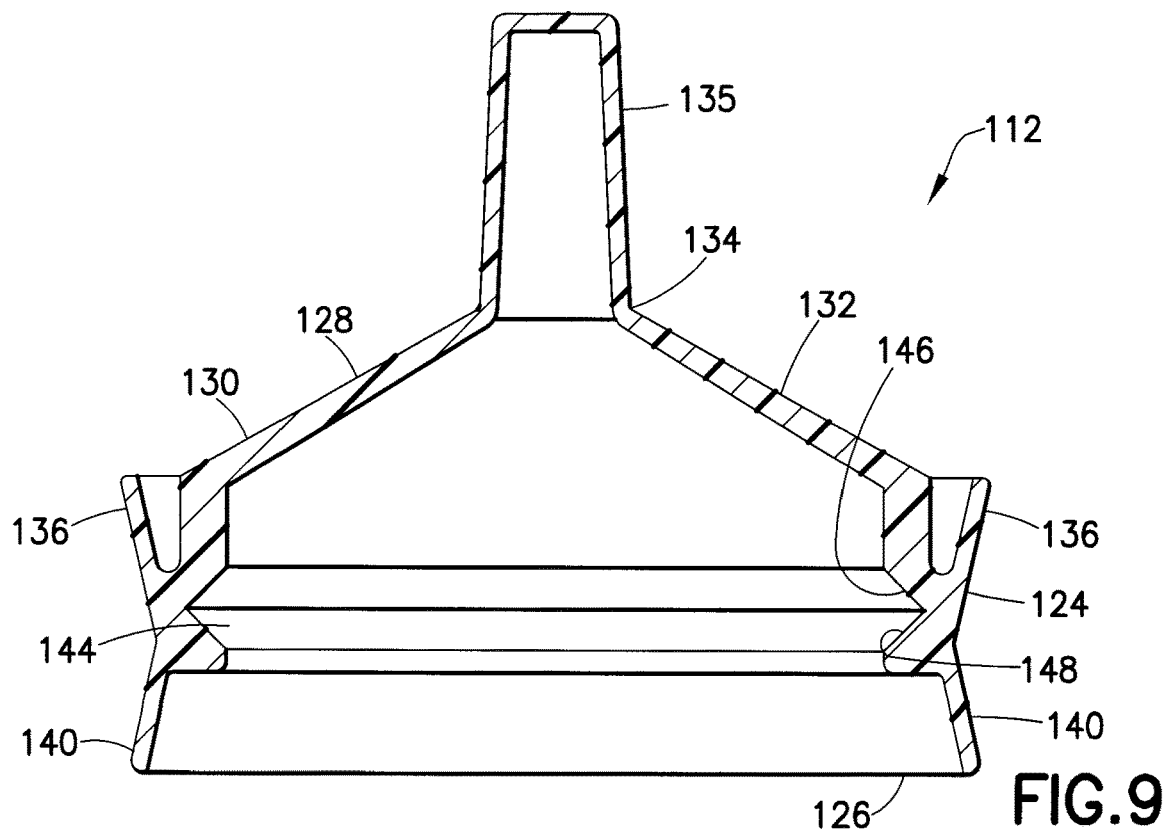
FIG. 9 is a cross-sectional side view of the stopper of FIG. 8 taken along line 9-9.
Figure 10:
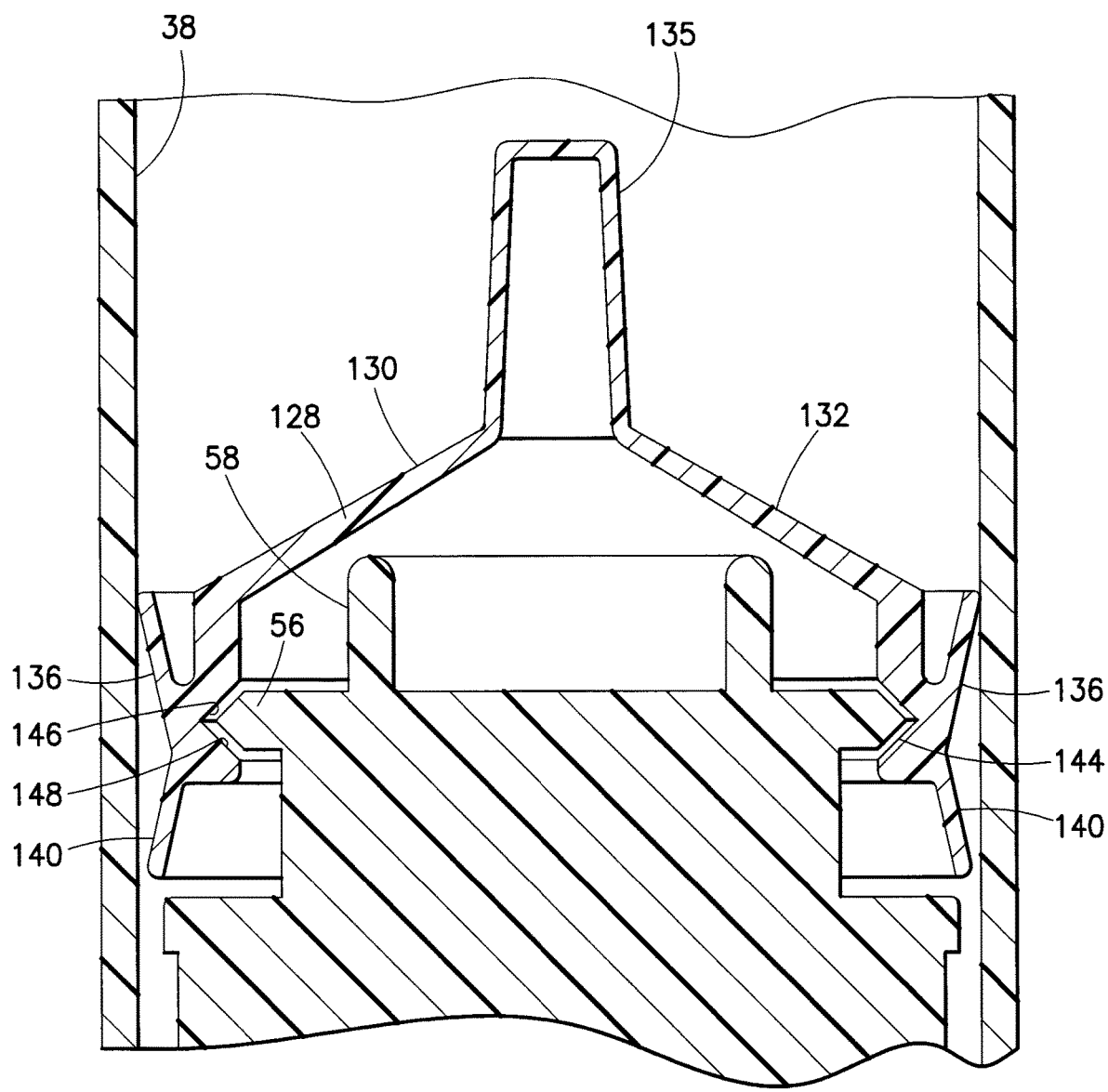
FIG. 10 is a cross-sectional side view of the stopper of FIG. 8 attached to a plunger rod and positioned within a syringe barrel.

With reference to FIGS. 8-10, a second embodiment of a stopper in accordance with the present invention, generally denoted as reference numeral 112, is illustrated. The stopper 112 includes a main body portion 124 defining an open rearward end 126 configured to receive the plunger rod 14 and a closed front end 128 that forms a flexible roof. The closed front end 128 of the main body portion 124 includes a first angled portion 130 and a second angled portion 132, which are both part of the same conical surface that extends to a tip 134. The tip 134 includes an extended portion 135 configured to fit inside a tip of the syringe barrel 16 to minimize the space in the syringe barrel 16 where unused medication remains after an injection has been completed. The extended portion 135 may also be used during the assembly of the syringe 10 to aid in properly orienting the stopper 112 within the syringe barrel 16.

A first perimetrical skirt 136 is provided that extends around an outer circumference of the main body portion 124 toward the closed front end 128. The primary purpose of the first perimetrical skirt 136 is to provide an "active seal" between the stopper body and an inner wall 38 of the syringe barrel 16 as discussed hereinabove. The stopper 112 also includes a second perimetrical skirt 140 extending around an outer circumference of the main body portion 124 toward the open rearward end 126. The primary purpose of the second perimetrical skirt 140 is to provide stability to the stopper 112 in an axial direction and to prevent tilting of the stopper 112. In addition, when fluid pressure is decreased inside the syringe barrel 116 during an aspiration, the second perimetrical skirt 140 is forced against the inner wall 38 of the syringe barrel 16, thereby providing a sealing pressure between the stopper 112 and the inner wall 38 of the syringe barrel 16.

As shown in FIG. 9, the main body portion 124 of the stopper 112 is substantially hollow and designed to receive an attachment portion 42 of the plunger rod 14. A notch 144 is provided that extends around an inner circumference of the main body portion 124. The notch 144 includes an upwardly angled portion 146 and a downwardly angled portion 148, thereby providing the notch 144 with a conical cross-sectional shape. However, the shape of notch 144 is not to be construed as limiting the present invention as other interfaces between the notch 144 and the attachment portion 42 of the plunger rod 14, such as linear or curved interfaces, could be utilized to provide the same function.

The notch 144 is configured to engage with the attachment portion 42 of the plunger rod such that during an injection, the upwardly angled portion 146 engages the attachment portion 42, thereby forcing the main body portion 124 in a radial direction (i.e., toward the barrel wall) such that a stronger seal is created between the main body portion 124 and the inner wall 38. During an aspiration, the downwardly angled portion 148 engages the attachment portion 42, thereby forcing the main body portion 124 in a radial direction (i.e., toward the barrel wall) such that a stronger seal is created between the main body portion 124 and the inner wall 38.

The plunger rod 14 used with the second embodiment of the stopper 112 is the same as the plunger rod 14 illustrated in FIGS. 5 and 6 and discussed hereinabove. In addition, the stopper 112 also includes an active sealing function such that when fluid pressure inside the syringe 10 increases due to injection, sealing pressure between the stopper 112 and the syringe barrel 16 also increases due to the three separate pressure activated actions discussed hereinabove with reference to FIG. 4A.

Figure 11:
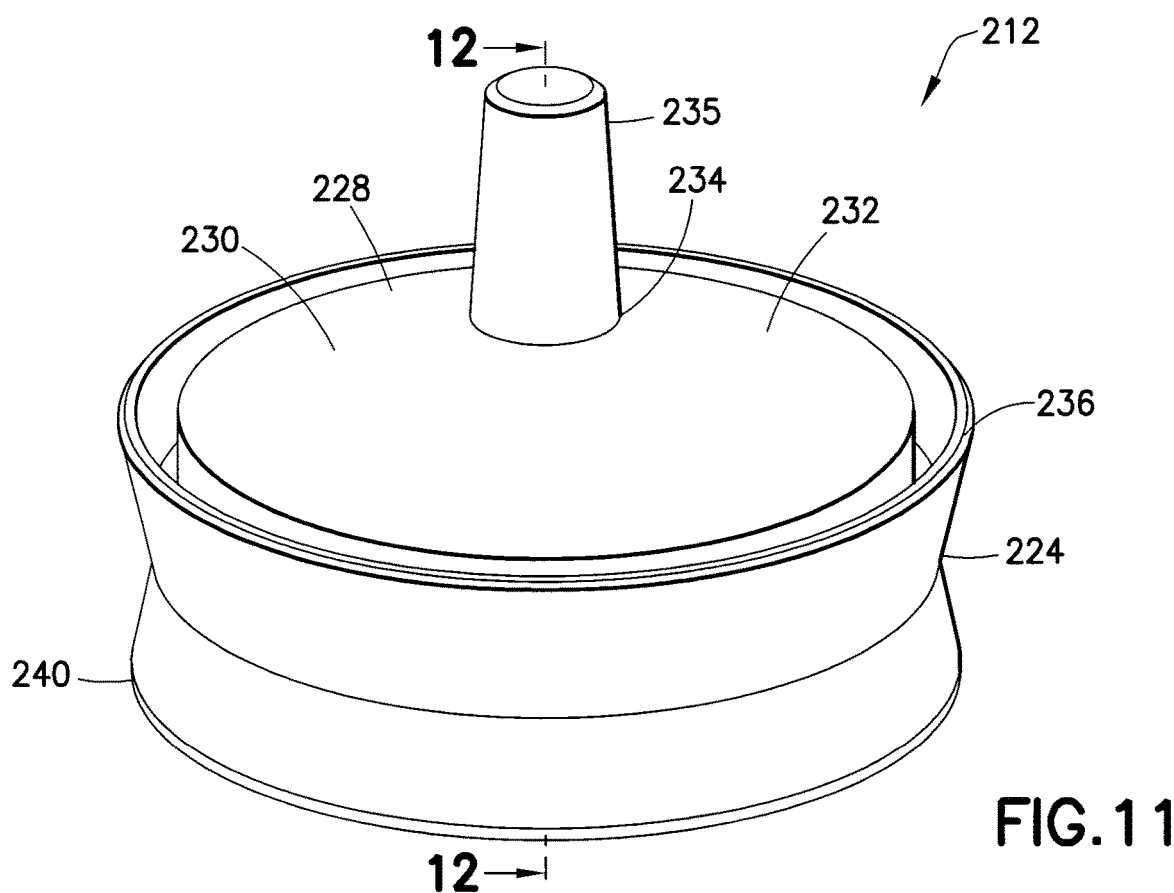
FIG. 11 is a perspective view of a stopper according to a third embodiment of the present invention.
Figure 12:
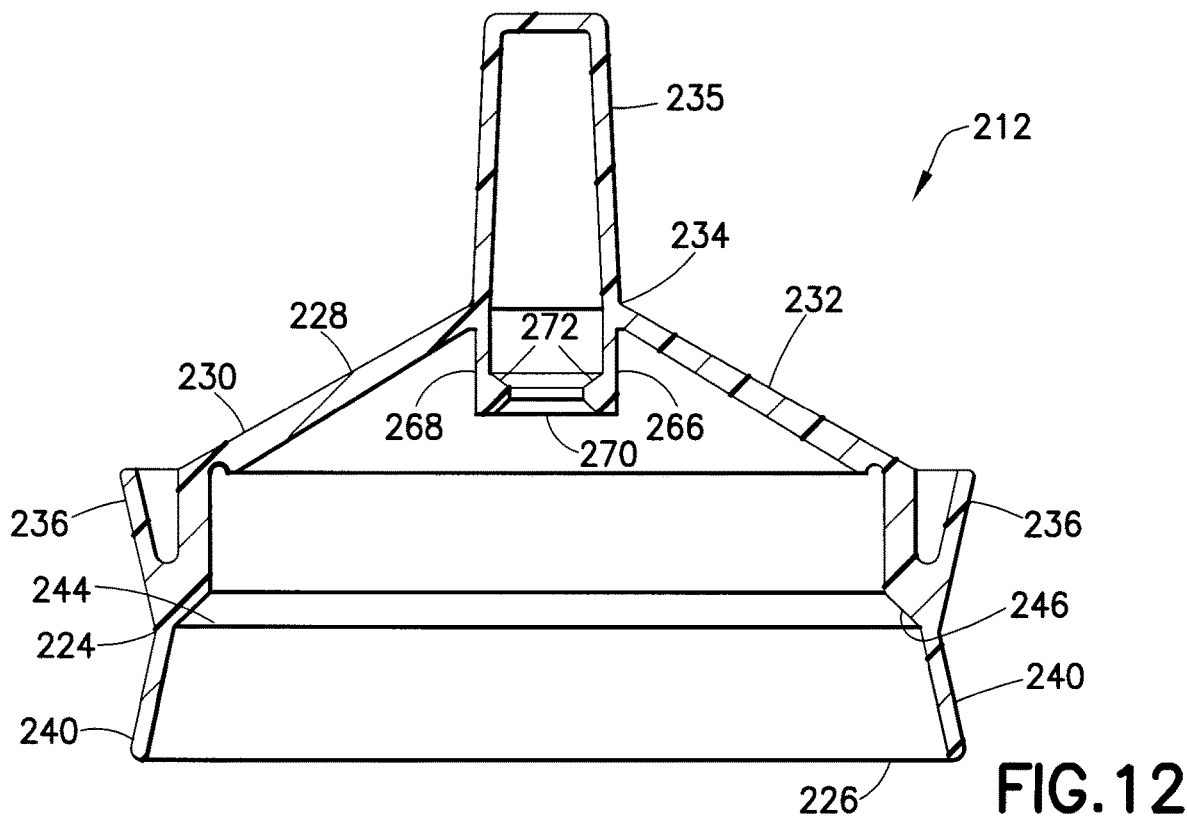
FIG. 12 is a cross-sectional side view of the stopper of FIG. 11 taken along line 12-12.
Figure 13:
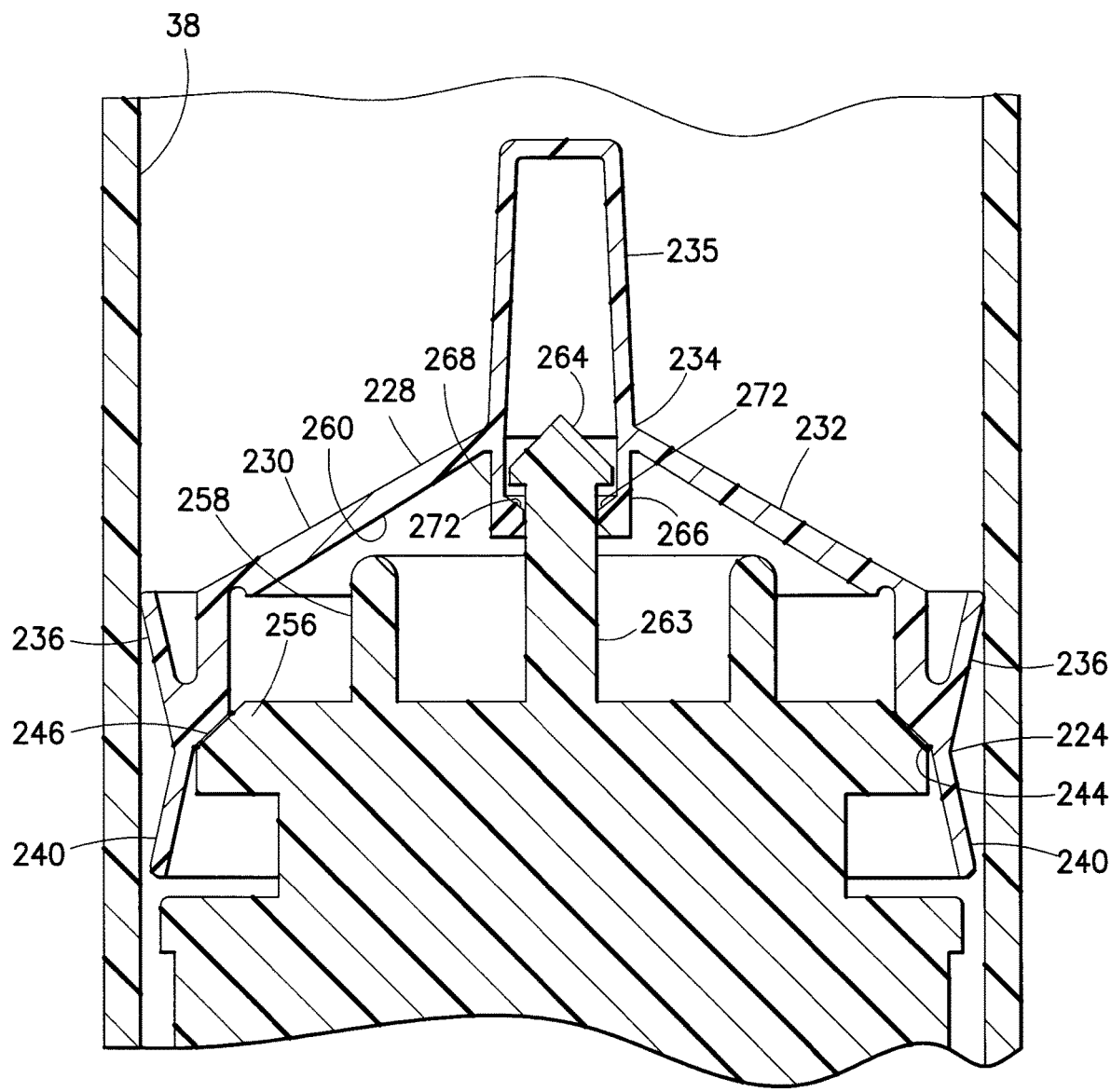
FIG. 13 is a cross-sectional side view of the stopper of FIG. 11 attached to a plunger rod and positioned within a syringe barrel.

With reference to FIGS. 11-13, a third embodiment of the stopper, generally denoted as reference numeral 212, is illustrated. The stopper 212 includes a main body portion 224 defining an open rearward end 226 configured to receive an alternative embodiment of plunger rod 214 (see FIGS. 14 and 15) and a closed front end 228 that forms a flexible roof. The closed front end 228 of the main body portion 224 includes a first angled portion 230 and a second angled portion 232, which are both part of the same conical surface that extends to a tip 234. The tip 234 includes an extended portion 235 configured to fit inside a tip of the syringe barrel 16 to minimize the space in the syringe barrel 16 where unused medication remains after an injection has been completed. The extended portion 135 may also be used during the assembly of the syringe 10 to aid in properly orienting the stopper 112 within the syringe barrel 16.

A first perimetrical skirt 236 is provided that extends around an outer circumference of the main body portion 224 toward the closed front end 228. The primary purpose of the first perimetrical skirt 236 is to provide an "active seal" between the stopper body and an inner wall 38 of the syringe barrel 16 as will be discussed in greater detail hereinafter. The stopper 212 also includes a second perimetrical skirt 240 extending around an outer circumference of the main body portion 224 toward the open rearward end 226. The primary purpose of the second perimetrical skirt 240 is to provide stability to the stopper 212 in an axial direction and to prevent tilting of the stopper 212. In addition, when fluid pressure is decreased inside the syringe barrel 16 during an aspiration, the second perimetrical skirt 240 is forced against the inner wall 38 of the syringe barrel 16, thereby providing a sealing pressure between the stopper 212 and the inner wall 38 of the syringe barrel 16.

As shown in FIG. 12, the main body portion 224 of the stopper 212 is substantially hollow and designed to receive an attachment portion 242 of plunger rod 214. A notch 244 is provided that extends around an inner circumference of the main body portion 224. The notch 244 includes an upwardly angled portion 246.

The notch 244 is configured to engage with the attachment portion 242 of the plunger rod such that during an injection, the upwardly angled portion 246 engages the attachment portion 242, thereby forcing the main body portion 224 in a radial direction (i.e., toward the barrel wall) such that a stronger seal is created between the main body portion 224 and the inner wall 38.

An extension 266 extending from the tip 234 toward the open rearward end 226 is also provided. The extension 266 has a substantially cylindrical hollow body portion 268 having an opening 270 at a bottom portion thereof facing the open rearward end 226 of stopper 212. The opening 270 has a diameter that is smaller than the diameter of the body portion 268, thereby creating a bearing surface 272 adjacent to the opening 270.

Figure 14:
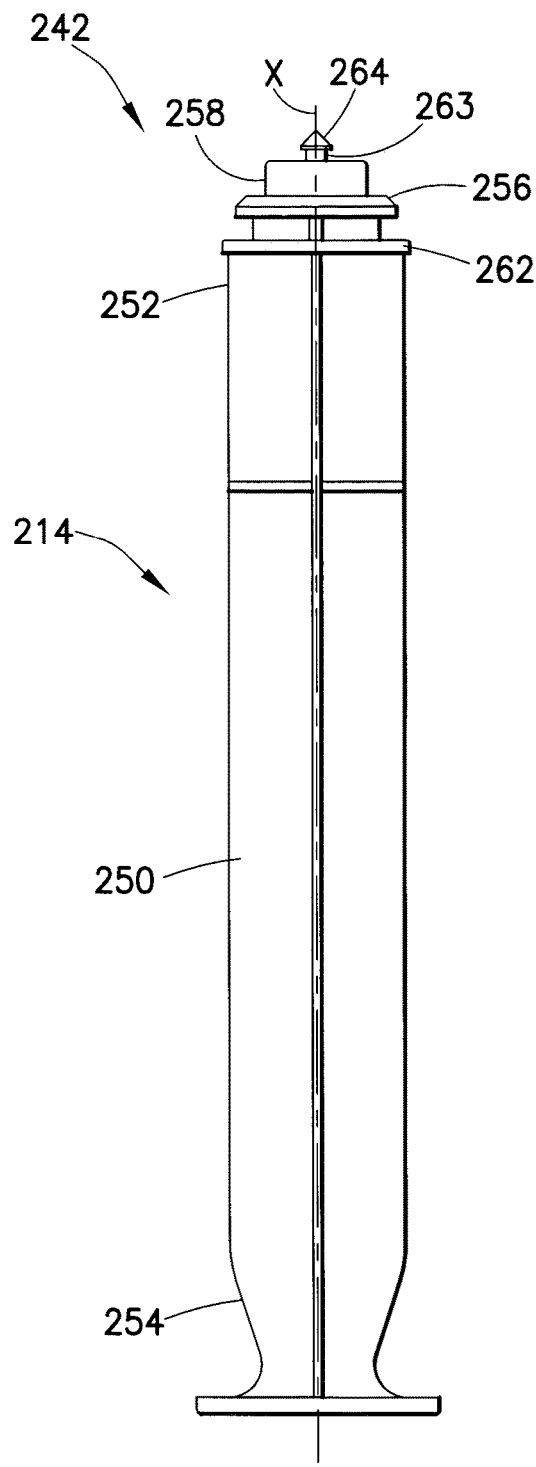
FIG. 14 is a side view of a plunger rod for use with the stopper of FIG. 11.
Figure 15:
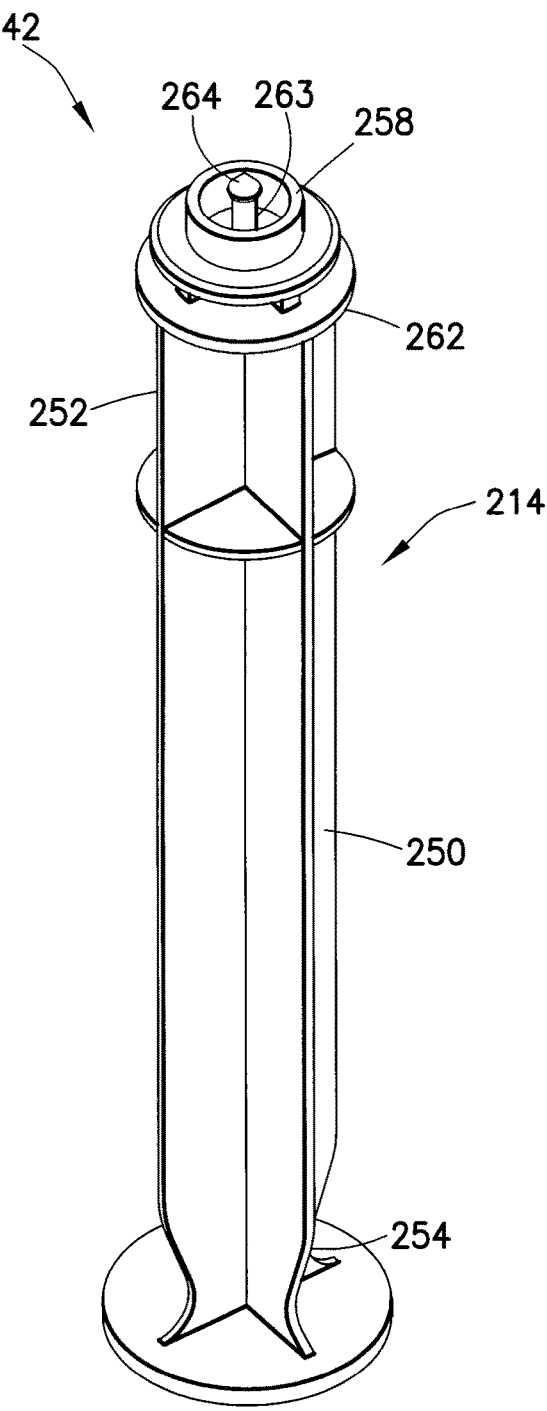
FIG. 15 is a perspective view of the plunger rod of FIG. 14.

With reference to FIGS. 14 and 15, the plunger rod 214 may include a syringe plunger body 250 having a front end 252 and a back end 254 extending along a longitudinal axis X. The attachment portion 242 is associated with the front end 252 of the syringe plunger body 250. The attachment portion 242 includes a tapered ring 256 designed to engage the notch 244 of the stopper 212 and an extension portion 258 configured to contact a lower surface 260 of the flexible roof of the closed front end 228 during an injection, thereby limiting the expansion of the flexible roof in the radial direction. The attachment portion 242 also includes a rod 263 having a conical head 264 extending from the front end 252 of the syringe plunger body 250 and configured to engage the extension 266 of the stopper 212 as discussed hereinafter.

The syringe plunger body 250 may also include a retaining ring 262 positioned adjacent to the open rearward end 226 of the main body portion 224 of the stopper 212. The retaining ring 262 is provided to prevent the plunger rod 214 from being removed from the syringe barrel 16. With reference to FIG. 13, when the plunger rod 214 is inserted into the stopper 212 through the open rearward end 226, the tapered ring 256 engages the notch 244 and the rod 263 is inserted into the opening 270 of the extension 266 such that the plunger rod 214 is locked in place and is prevented from separating from the stopper 212.

With continued reference to FIG. 13, the rigid plastic stopper 212 includes an active sealing function such that when fluid pressure inside the syringe 10 increases due to injection, sealing pressure between the stopper 212 and the syringe barrel 16 also increases due to three separate pressure activated actions as described in detail hereinabove with reference to the first and second embodiments. During an aspiration, the conical head 264 of the rod 263 contacts the bearing surface 272 of the extension 266 causing the flexible roof of the main body portion 224 to expand in the radial direction toward the inner wall 38 of the syringe barrel 216 as a result of the negative pressure pulling the flexible roof up. Such a configuration is suitable for larger syringe sizes (10 ml-60 ml) where a larger roof area is exposed to negative pressure.

Figure 16:
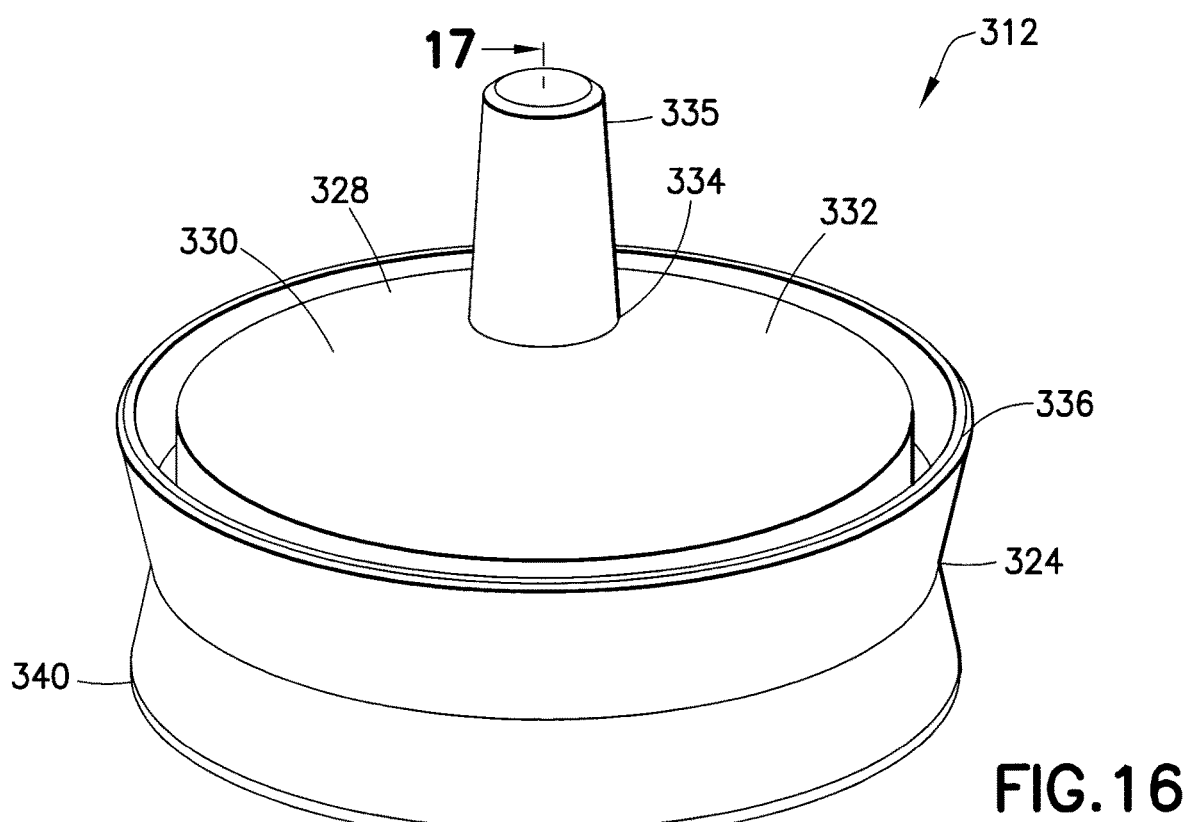
FIG. 16 is a perspective view of a stopper according to a fourth embodiment of the present invention.
Figure 17:
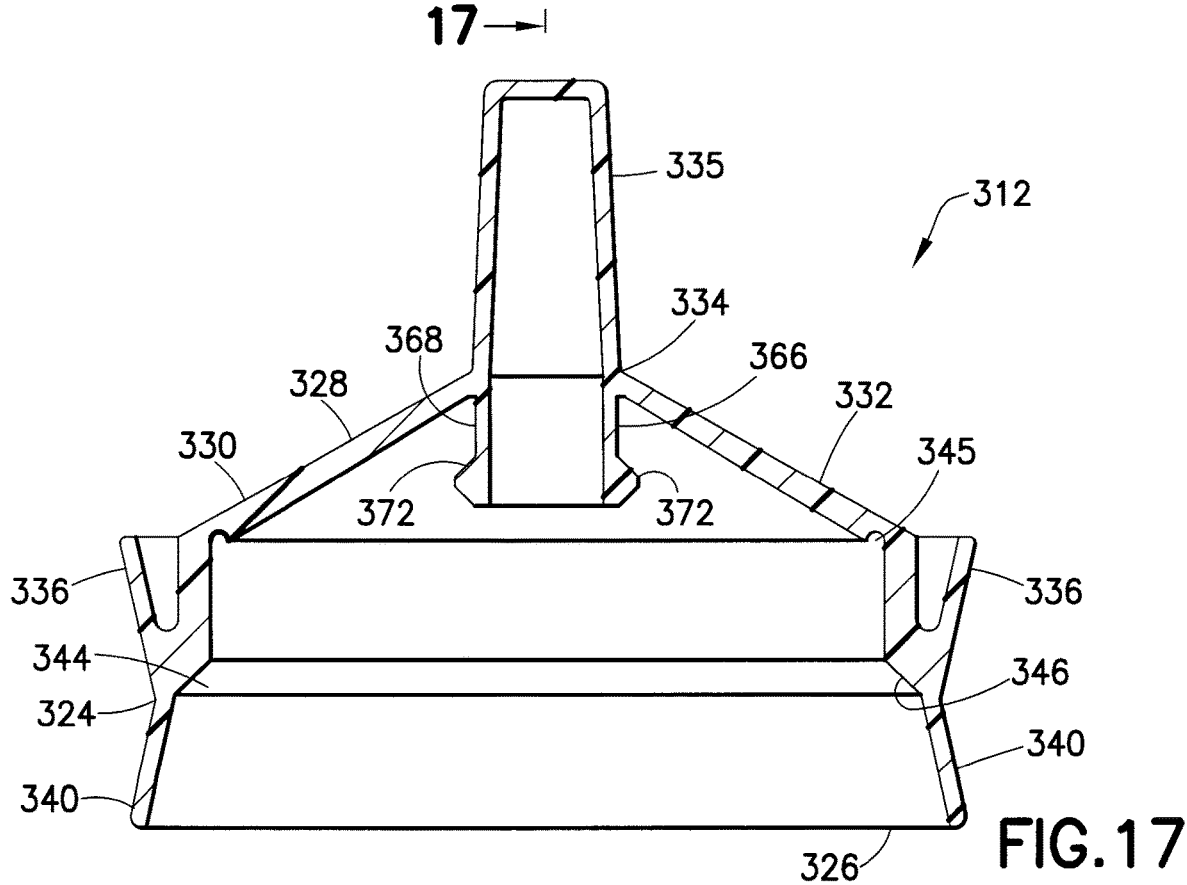
FIG. 17 is a cross-sectional side view of the stopper of FIG. 16 taken along line 17-17.
Figure 18:
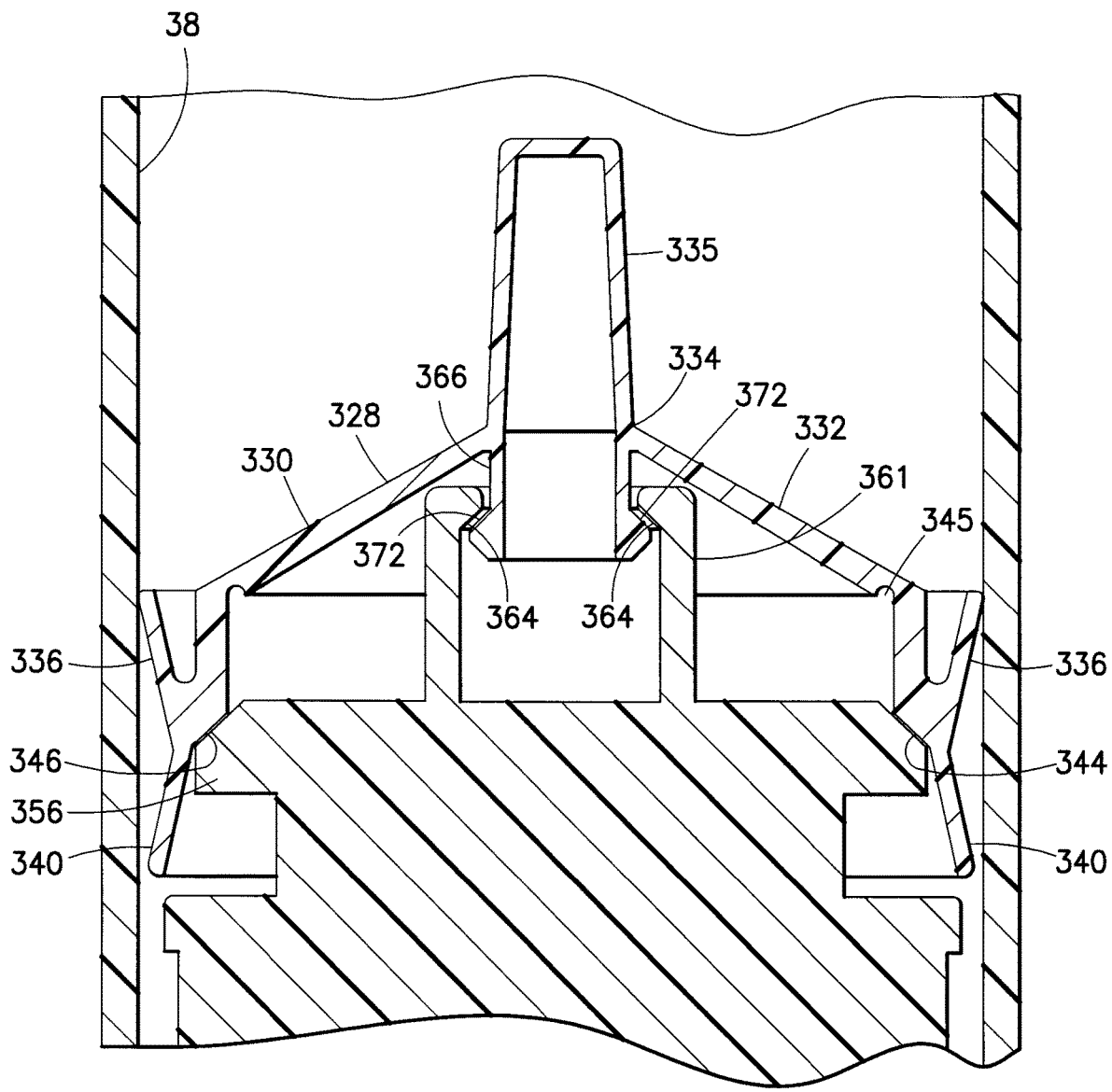
FIG. 18 is a cross-sectional side view of the stopper of FIG. 16 attached to a plunger rod and positioned within a syringe barrel.

With reference to FIGS. 16-18, a fourth embodiment of the stopper, generally denoted as reference numeral 312, is illustrated. The stopper 312 includes a main body portion 324 defining an open rearward end 326 configured to receive an alternative embodiment of plunger rod 314 (see FIGS. 19 and 20) and a closed front end 328 that forms a flexible roof. The closed front end 328 of the main body portion 324 includes a first angled portion 330 and a second angled portion 332, which are both part of the same conical surface that extends to a tip 334. The tip 334 includes an extended portion 335 configured to fit inside a tip of the syringe barrel 16 to minimize the space in the syringe barrel 16 where unused medication remains after an injection has been completed. The extended portion 335 may also be used during the assembly of the syringe 10 to aid in properly orienting the stopper 312 within the syringe barrel 16.

A first perimetrical skirt 336 is provided that extends around an outer circumference of the main body portion 324 toward the closed front end 328. The primary purpose of the first perimetrical skirt 336 is to provide an "active seal" between the stopper body and an inner wall 38 of the syringe barrel 16 as will be discussed in greater detail hereinafter. The stopper 312 also includes a second perimetrical skirt 340 extending around an outer circumference of the main body portion 324 toward the open rearward end 326. The primary purpose of the second perimetrical skirt 340 is to provide stability to the stopper 312 in an axial direction and to prevent tilting of the stopper 312. In addition, when fluid pressure is decreased inside the syringe barrel 16 during an aspiration, the second perimetrical skirt 340 is forced against the inner wall 38 of the syringe barrel 16, thereby providing a sealing pressure between the stopper 312 and the inner wall 38 of the syringe barrel 16.

As shown in FIG. 17, the main body portion 324 of the stopper 312 is substantially hollow and designed to receive an attachment portion 342 of plunger rod 314. A notch 344 is provided that extends around an inner circumference of the main body portion 324. The notch 344 includes an upwardly angled portion 346. A groove 345 may be provided along an edge of the flexible roof of the main body portion 324 to tune the stiffness of the flexible roof and/or the main body portion 324 in order to achieve a desired flexing response.

The notch 344 is configured to engage with the attachment portion 342 of the plunger rod such that during an injection, the upwardly angled portion 346 engages the attachment portion 342, thereby forcing the main body portion 324 in a radial direction (i.e., toward the barrel wall) such that a stronger seal is created between the main body portion 324 and the inner wall 38.

An extension 366 extending from the tip 334 toward the open rearward end 326 is also provided. The extension 366 has a substantially cylindrical hollow body portion 368 having bearing surface 372 extending from and around an outer diameter thereof.

Figure 19:
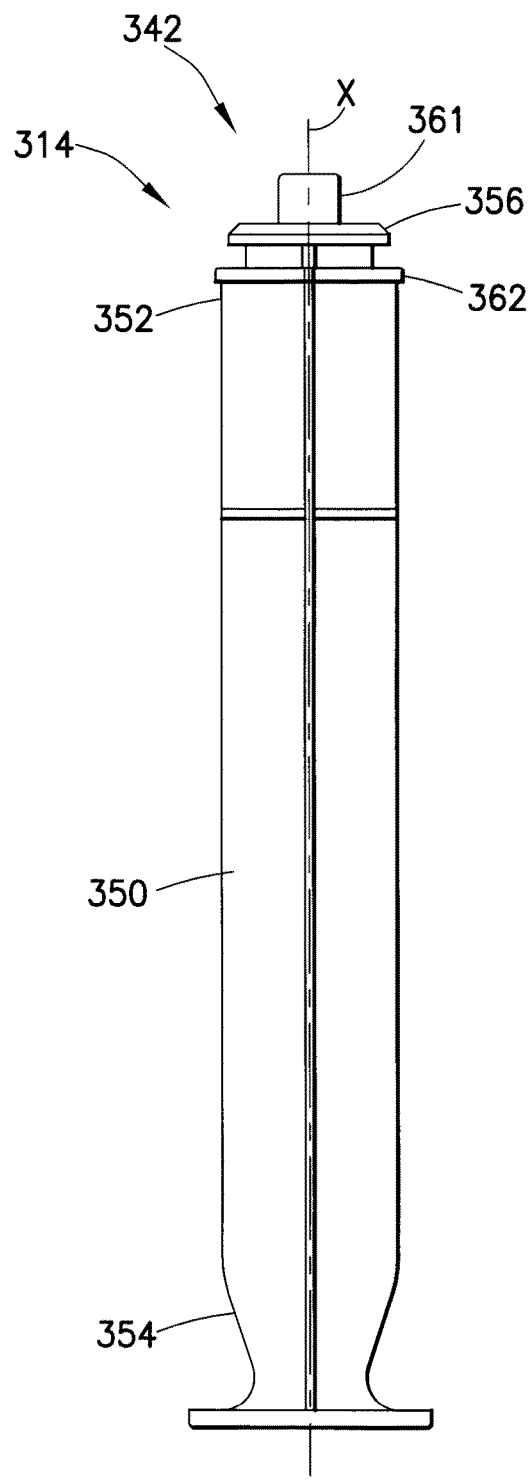
FIG. 19 is a side view of a plunger rod for use with the stopper of FIG. 16.
Figure 20:
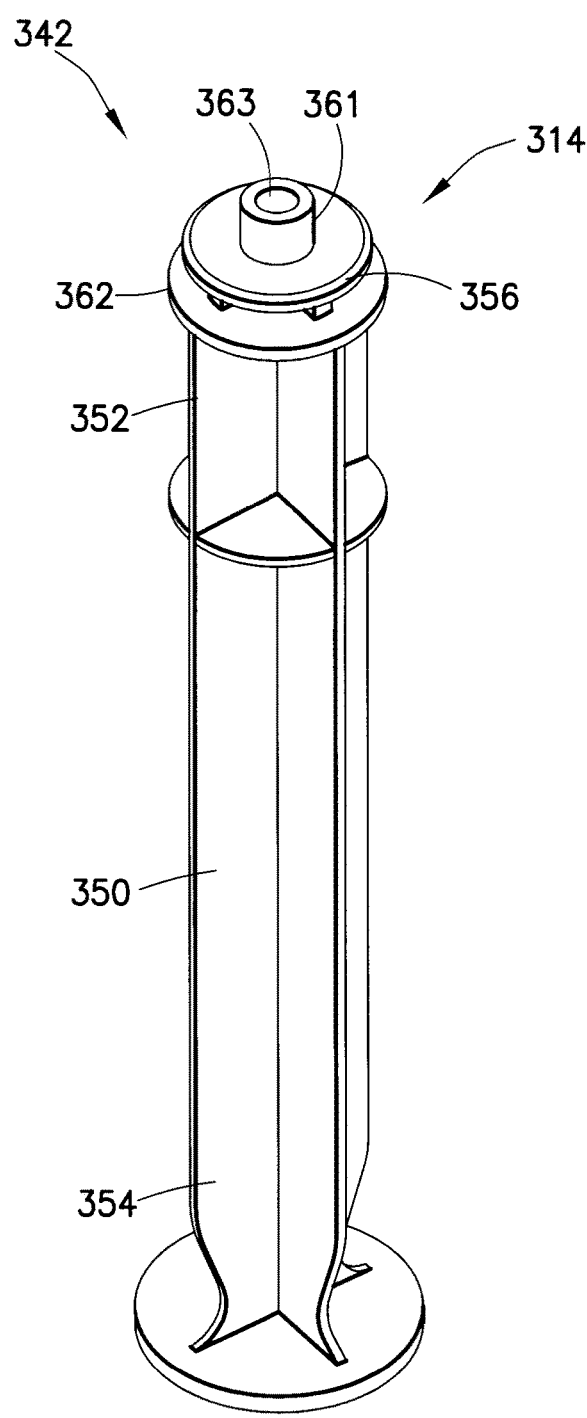
FIG. 20 is a perspective view of the plunger rod of FIG. 19.

With reference to FIGS. 19 and 20, the plunger rod 314 includes a syringe plunger body 350 having a front end 352 and a back end 354 extending along a longitudinal axis X. The attachment portion 342 is associated with the front end 352 of the syringe plunger body 350. The attachment portion 342 includes a tapered ring 356 designed to engage the notch 244 of the stopper 312 and a cylindrical body 361 having an opening 363 extending from the front end 352 of the syringe plunger body 350 and configured to engage the extension 366 of the stopper 312 as discussed hereinafter. The opening 363 has a diameter that is smaller than the diameter of the body 361, thereby creating a bearing surface 364 adjacent to the opening 363.

The syringe plunger body 350 may also include a retaining ring 362 positioned adjacent to the open rearward end 326 of the main body portion 324 of the stopper 312. The retaining ring 362 is provided to prevent the plunger rod 314 from being removed from the syringe barrel 16. With reference to FIG. 18, when the plunger rod 314 is inserted into the stopper 312 through the open rearward end 326, the tapered ring 356 engages the notch 344 and the extension 366 is inserted into the opening 363 of the cylindrical body 361 such that the plunger rod 314 is locked in place and is prevented from separating from the stopper 312.

With continued reference to FIG. 18, the rigid plastic stopper 312 includes an active sealing function such that when fluid pressure inside the syringe 10 increases due to injection, sealing pressure between the stopper 312 and the syringe barrel 16 also increases due to three separate pressure activated actions as described in detail hereinabove with reference to the first through third embodiments. During an aspiration, the bearing surface 364 of the cylindrical body 361 contacts the bearing surface 372 of the extension 366 causing the flexible roof of the main body portion 324 to expand in the radial direction toward the inner wall 38 of the syringe barrel 216 as a result of the negative pressure pulling the flexible roof up. Such a configuration is also suitable for larger syringe sizes (10 ml-60 ml) where a larger roof area is exposed to negative pressure.

Figure 21:
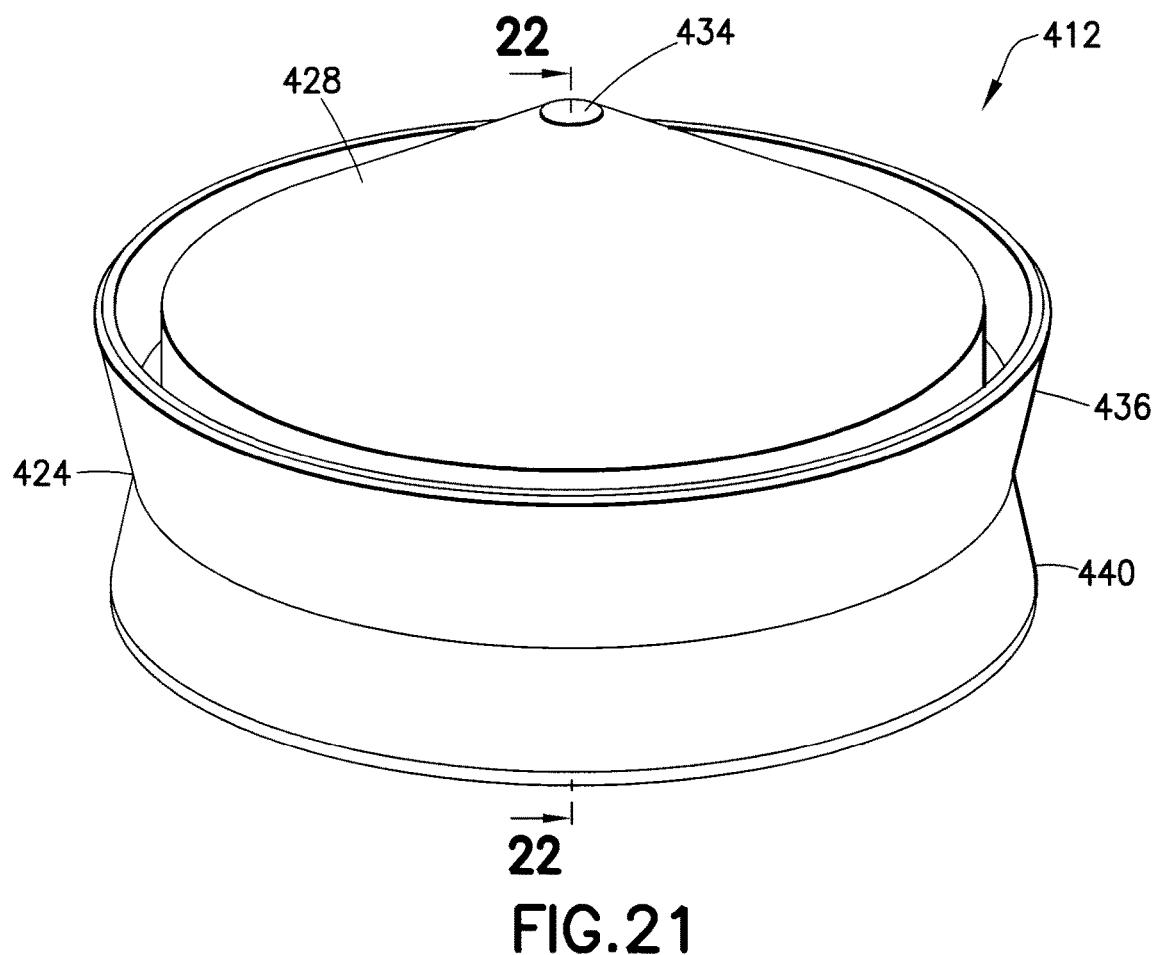
FIG. 21 is a perspective view of a stopper according to a fifth embodiment of the present invention.
Figure 22:
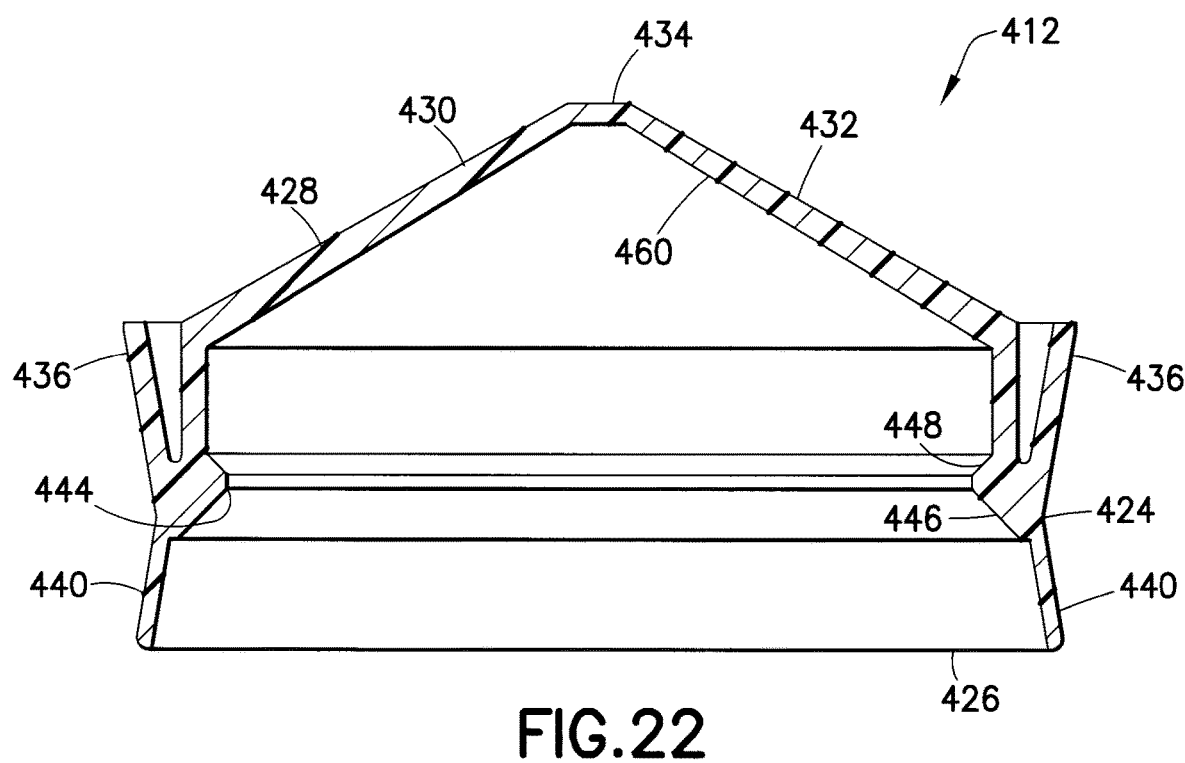
FIG. 22 is a cross-sectional side view of the stopper of FIG. 21 taken along line 22-22.
Figure 23:
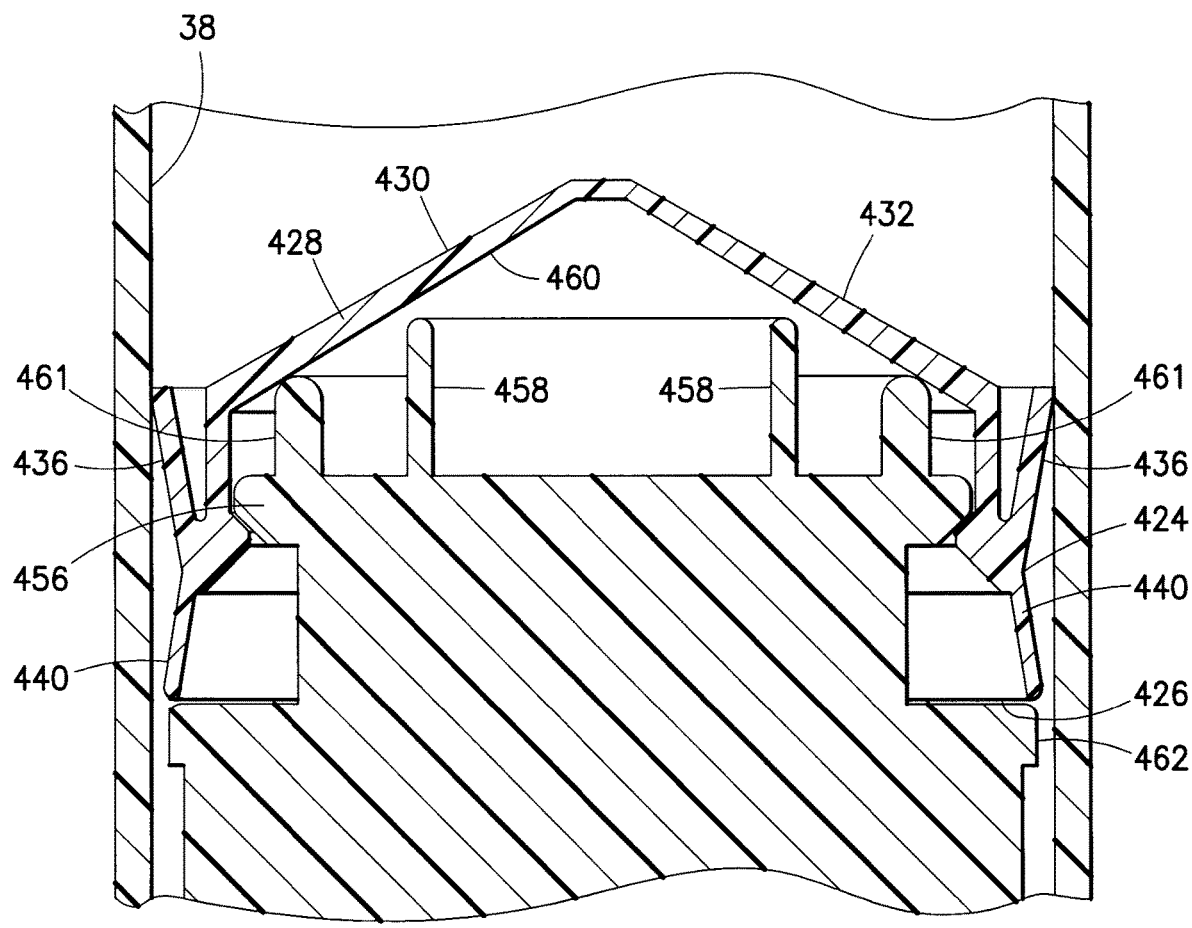
FIG. 23 is a cross-sectional side view of the stopper of FIG. 21 attached to a plunger rod and positioned within a syringe barrel.

With reference to FIGS. 21-23, a fifth embodiment of the stopper, generally denoted as reference numeral 412, is illustrated. The stopper 412 includes a main body portion 424 defining an open rearward end 426 configured to receive the plunger rod 414 (see FIGS. 24 and 25) and a closed front end 428 that forms a flexible roof. The closed front end 428 of the main body portion 424 includes a first angled portion 430 and a second angled portion 432, which are both part of the same conical surface that extends to a tip 434, thereby providing the closed front end 428 with a substantially conical appearance.

A first perimetrical skirt 436 is provided that extends around an outer circumference of the main body portion 424 toward the closed front end 428. The primary purpose of the first perimetrical skirt 436 is to provide an "active seal" between the stopper body and an inner wall 38 of the syringe barrel 16 as discussed hereinabove. The stopper 412 also includes a second perimetrical skirt 440 extending around an outer circumference of the main body portion 424 toward the open rearward end 426. The primary purpose of the second perimetrical skirt 440 is to provide stability to the stopper 412 in an axial direction and to prevent tilting of the stopper 412. In addition, when fluid pressure is decreased inside the syringe barrel 416 during an aspiration, the second perimetrical skirt 440 is forced against the inner wall 38 of the syringe barrel 16, thereby providing a sealing pressure between the stopper 412 and the inner wall 38 of the syringe barrel 16.

As shown in FIG. 23, the main body portion 424 of the stopper 412 is substantially hollow and designed to receive an attachment portion 442 of plunger rod 414. A flange 444 extends toward the center of stopper 412 and around an inner circumference of the main body portion 424. The flange 444 includes an upwardly angled portion 446 and a downwardly angled portion 448.

The flange 444 is configured to engage with the attachment portion 442 of the plunger rod 414 such that during an aspiration, the downwardly angled portion 448 engages the attachment portion 442, thereby forcing the main body portion 424 in a radial direction (i.e., toward barrel wall) such that a stronger seal is created between the main body portion 424 and the inner wall 38.

Figure 24:
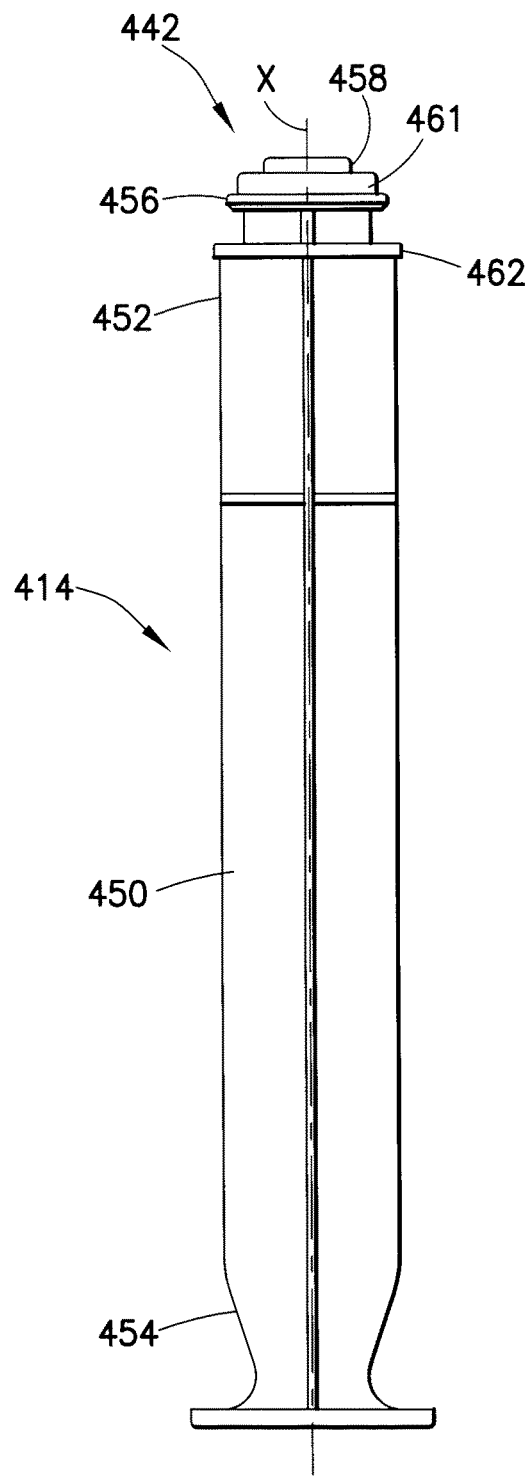
FIG. 24 is a side view of a plunger rod for use with the stopper of FIG. 21.
Figure 25:
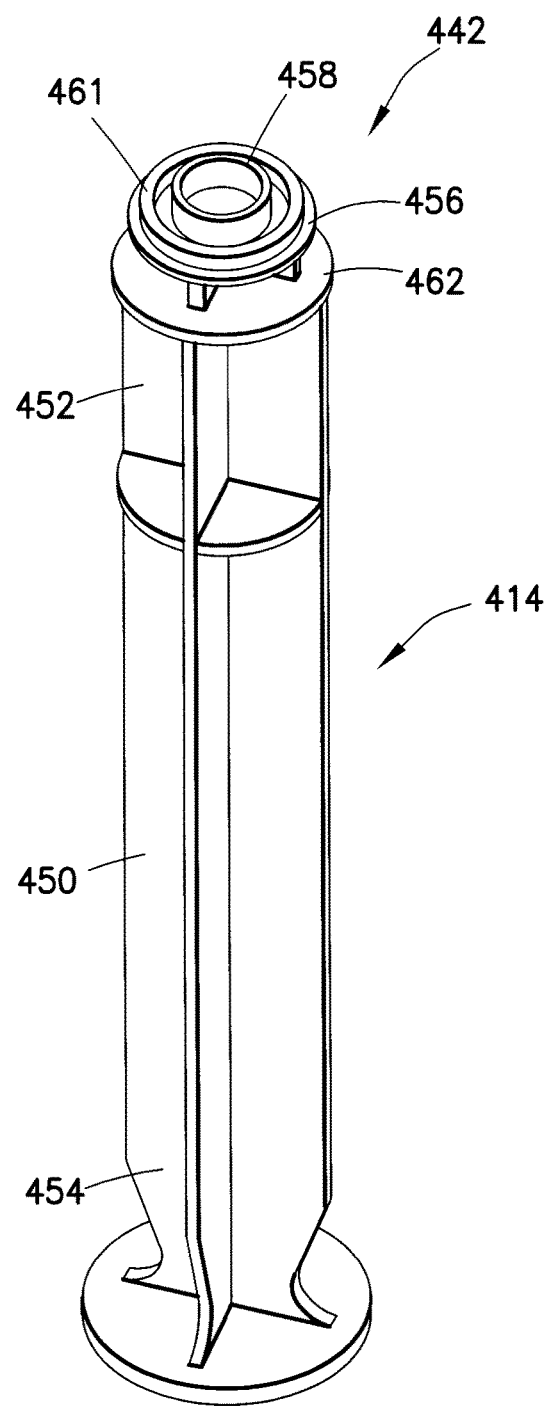
FIG. 25 is a perspective view of the plunger rod of FIG. 24.

With reference to FIGS. 24 and 25, the plunger rod 414 may include a syringe plunger body 450 having a front end 452 and a back end 454 extending along a longitudinal axis X. The attachment portion 442 is associated with the front end 452 of the syringe plunger body 450. The attachment portion 442 includes a first ring 456 designed to engage the flange 444 of the stopper 412 and an extension portion 458 configured to contact a lower surface 460 of the flexible roof of the closed front end 428 during an injection, thereby limiting the expansion of the flexible roof in the radial direction. The attachment portion 442 also includes a second ring 461 provided at the front end 452. The second ring 461 is configured such that, during an injection, an upper surface of the second ring 461 engages the lower surface 460 of the flexible roof, thereby forcing the main body portion 424 in a radial direction (i.e., toward the barrel wall) such that a stronger seal is created between the main body portion 424 and the inner wall 38.

The syringe plunger body 450 may also include a retaining ring 462 positioned adjacent to the open rearward end 426 of the main body portion 424 of the stopper 412. The retaining ring 462 is provided to prevent the plunger rod 414 from being removed from the syringe barrel 16. With reference to FIG. 23, when the plunger rod 414 is inserted into the stopper 412 through the open rearward end 426, the first ring 456 engages the flange 444 such that the plunger rod 414 is locked in place and is prevented from separating from the stopper 412.

Figure 26:
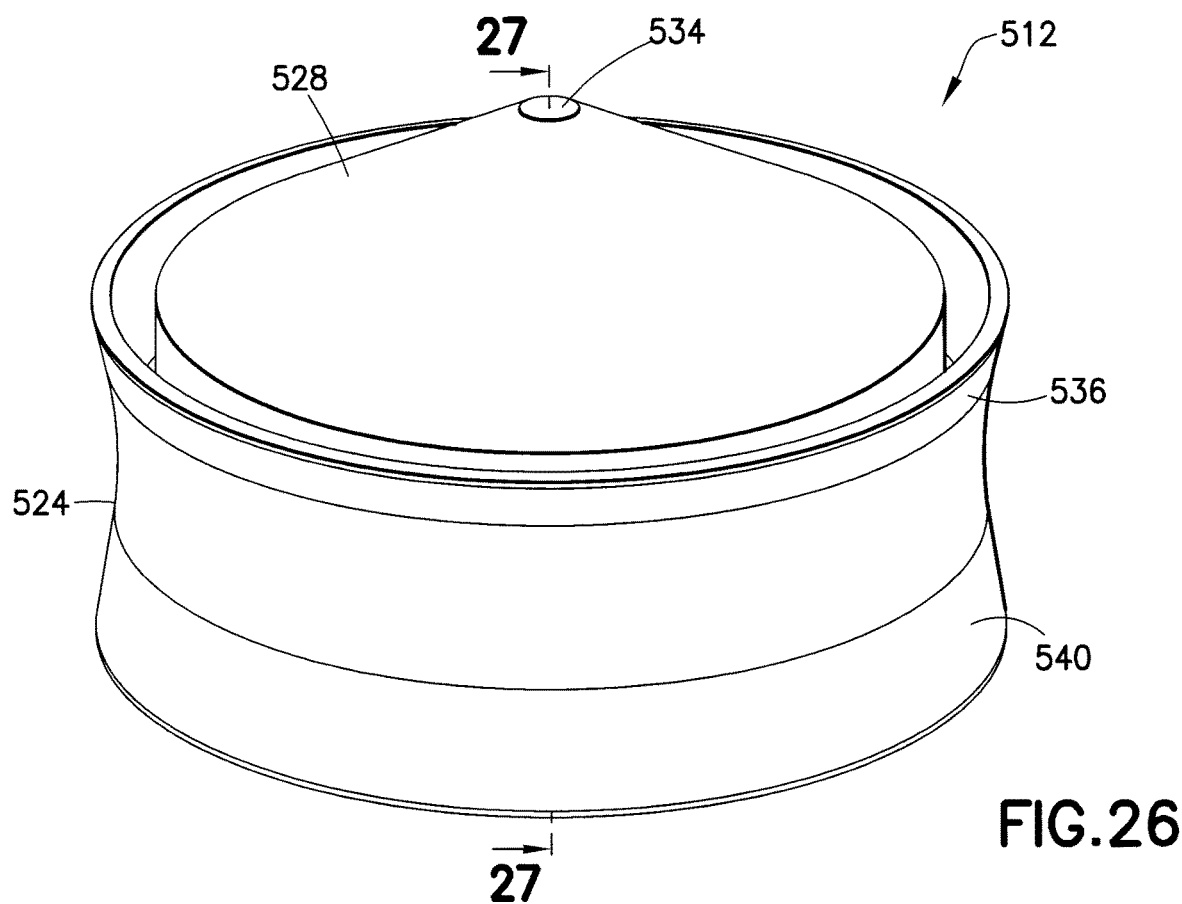
FIG. 26 is a perspective view of a stopper according to a sixth embodiment of the present invention.
Figure 27:
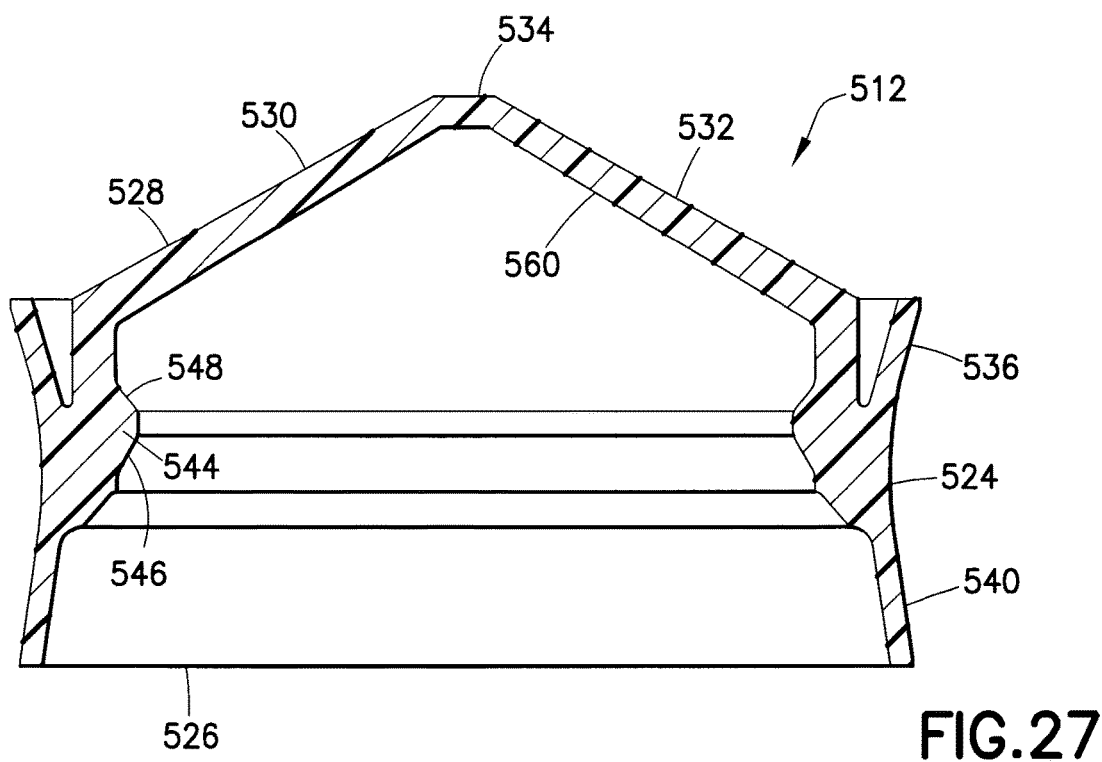
FIG. 27 is a cross-sectional side view of the stopper of FIG. 26 taken along line 27-27.
Figure 28:
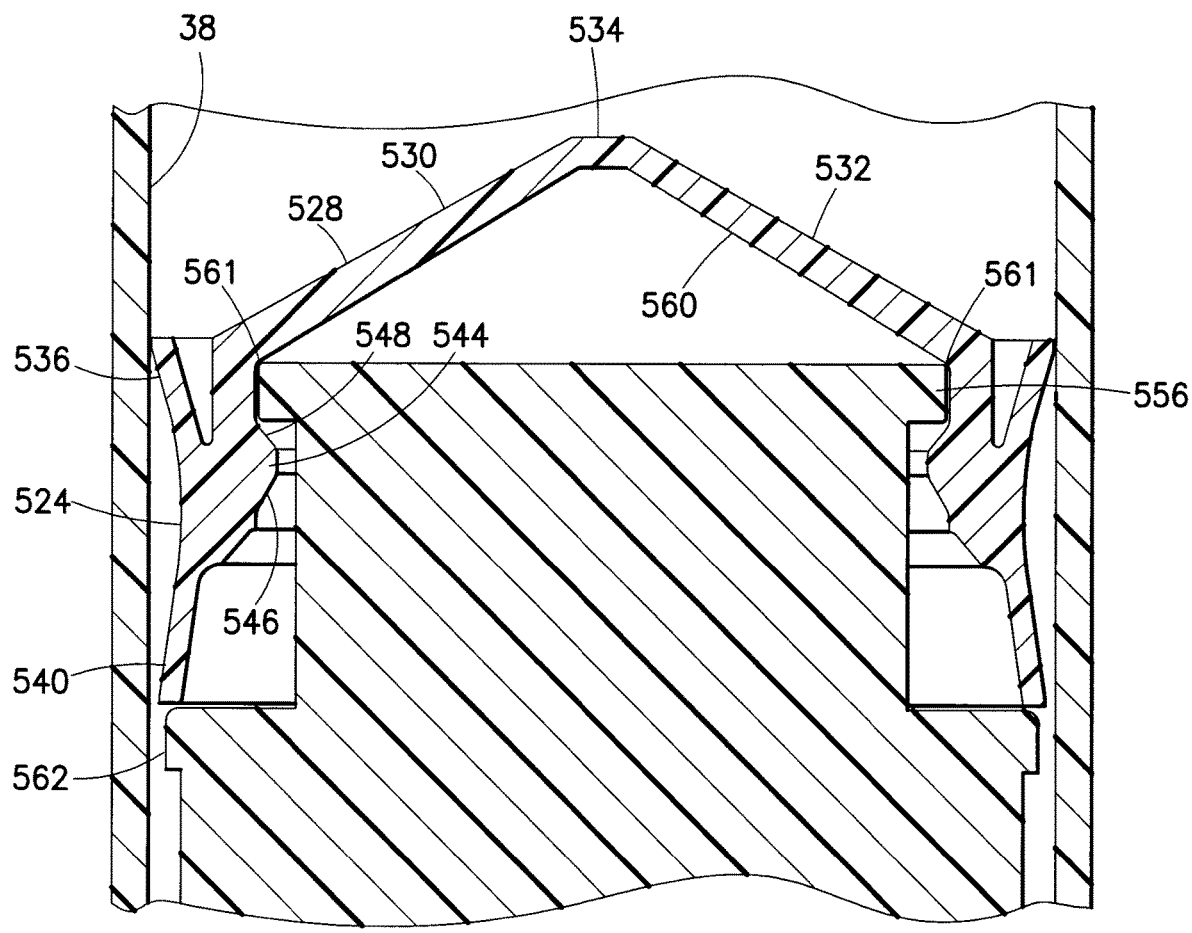
FIG. 28 is a cross-sectional side view of the stopper of FIG. 26 attached to a plunger rod and positioned within a syringe barrel.

With reference to FIGS. 26-28, a sixth embodiment of the stopper, generally denoted as reference numeral 512, is illustrated. The stopper 512 includes a main body portion 524 defining an open rearward end 526 configured to receive the plunger rod 514 (see FIGS. 29 and 30) and a closed front end 528 that forms a flexible roof. The closed front end 528 of the main body portion 524 includes a first angled portion 530 and a second angled portion 532, which are both part of the same conical surface that extends to a tip 534, thereby providing the closed front end 528 with a substantially conical appearance.

A first perimetrical skirt 536 is provided that extends around an outer circumference of the main body portion 524 toward the closed front end 528. The primary purpose of the first perimetrical skirt 536 is to provide an "active seal" between the stopper body and an inner wall 38 of the syringe barrel 16 as discussed hereinabove. The stopper 512 also includes a second perimetrical skirt 540 extending around an outer circumference of the main body portion 524 toward the open rearward end 526. The primary purpose of the second perimetrical skirt 540 is to provide stability to the stopper 512 in an axial direction and to prevent tilting of the stopper 512. In addition, when fluid pressure is decreased inside the syringe barrel 16 during an aspiration, the second perimetrical skirt 540 is forced against the inner wall 38 of the syringe barrel 16, thereby providing a sealing pressure between the stopper 512 and the inner wall 38 of the syringe barrel 16.

As shown in FIG. 27, the main body portion 524 of the stopper 512 is substantially hollow and designed to receive an attachment portion 542 of plunger rod 514. A flange 544 extends toward the center of stopper 512 and around an inner circumference of the main body portion 524. The flange 544 includes an upwardly angled portion 546 and a downwardly angled portion 548.

The flange 544 is configured to engage with the attachment portion 542 of the plunger rod 514 such that during an aspiration, the downwardly angled portion 548 engages the attachment portion 542, thereby forcing the main body portion 524 in a radial direction (i.e., toward barrel wall) such that a stronger seal is created between the main body portion 524 and the inner wall 38.

Figure 29:
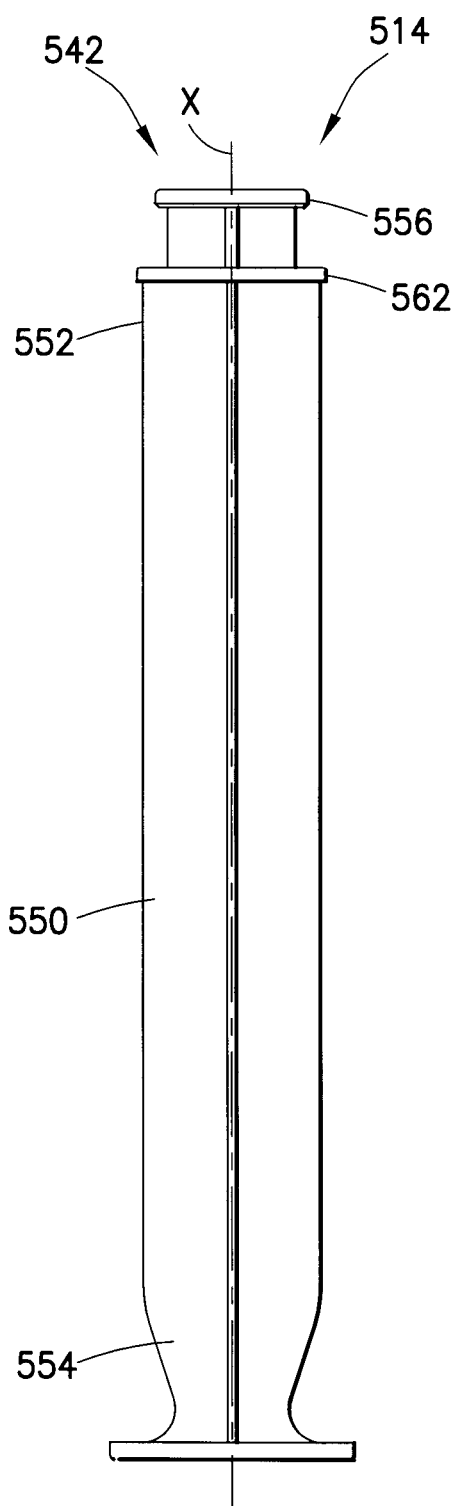
FIG. 29 is a side view of a plunger rod for use with the stopper of FIG. 26.
Figure 30:
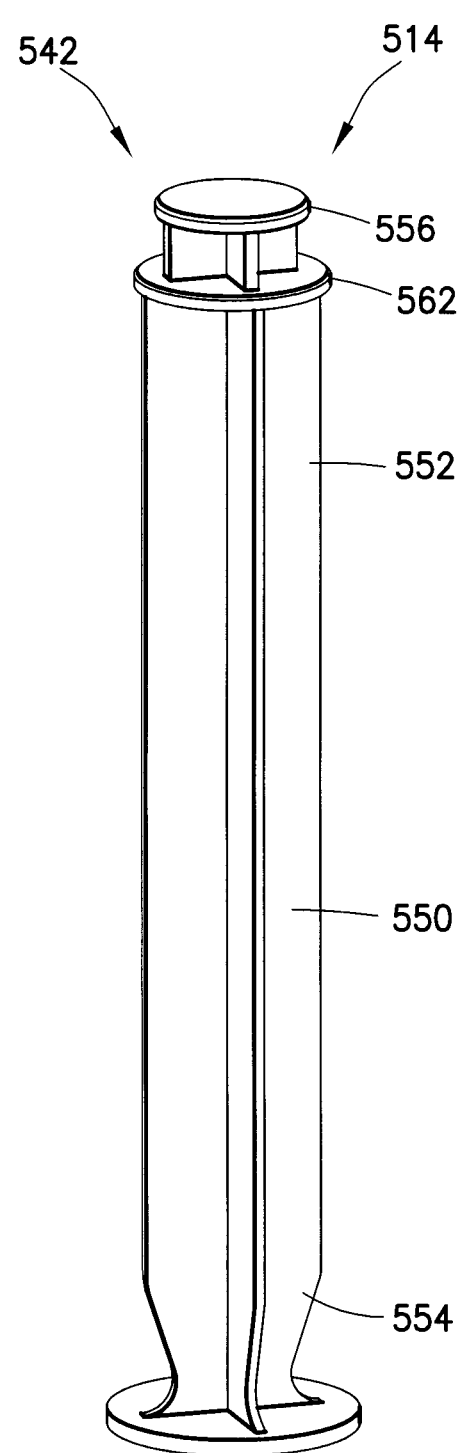
FIG. 30 is a perspective view of the plunger rod of FIG. 29.

With reference to FIGS. 29 and 30, the plunger rod 514 may include an a syringe plunger body 550 having a front end 552 and a back end 554 extending along a longitudinal axis X. The attachment portion 542 is associated with the front end 552 of the syringe plunger body 550. The attachment portion 542 includes a disk 556 designed to engage the flange 544 of the stopper 512. The disk 556 also includes a tapered surface 561 provided at the front end 552. The tapered surface 561 is configured such that during an injection, it engages the lower surface 560 of the flexible roof, thereby forcing the main body portion 524 in a radial direction (i.e., toward the barrel wall) such that a stronger seal is created between the main body portion 524 and the inner wall 38.

The syringe plunger body 550 may also include a retaining ring 562 positioned adjacent to the open rearward end 526 of the main body portion 524 of the stopper 512. The retaining ring 562 is provided to prevent the plunger rod 514 from being removed from the syringe barrel 16. With reference to FIG. 28, when the plunger rod 514 is inserted into the stopper 512 through the open rearward end 526, the disk 556 engages the flange 544 such that the plunger rod 514 is locked in place and is prevented from separating from the stopper 512.

Figure 31:
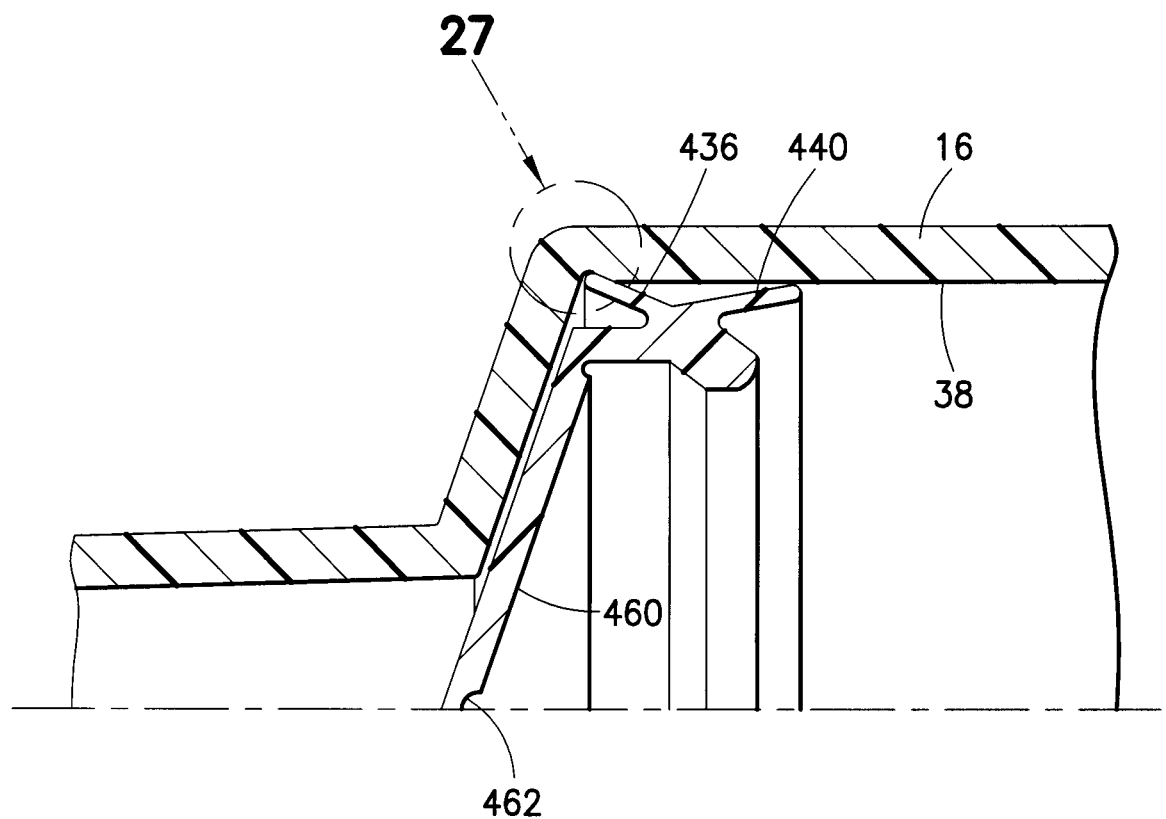
FIG. 31 is a cross-sectional view of the stopper of FIG. 21 positioned at the end of a syringe barrel.
Figure 32:
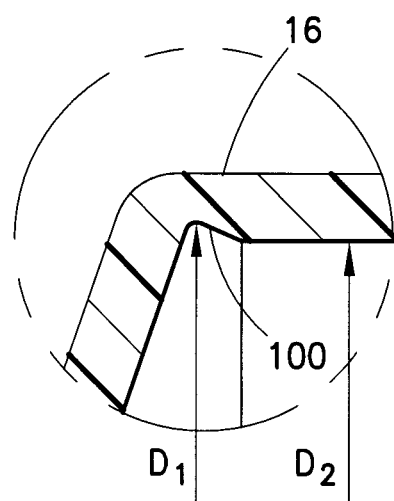
FIG. 32 is a portion of FIG. 31 enlarged for magnification purposes.

With reference to FIGS. 31 and 32, the syringe barrel 16 may include an area 100 near the fluid dispensing end thereof having an inner diameter $D_1$ that is greater than an inner diameter $D_2$ of remaining areas of the syringe barrel 16. This area is configured to receive the first perimetrical skirt 436 when the first perimetrical skirt 436 is positioned adjacent thereto, such as during storage. During storage, polymer creep phenomena (i.e., permanent deformation/relaxation) occurs on the outer diameter of first perimetrical skirt 436 due to the initial interference and contact stress between the stopper 412 and barrel 16. By providing such an area 100, it can be ensured that the first perimetrical skirt 436 will creep/adjust into the area 100, which has a diameter $D_1$ that is larger than the diameter $D_2$ of the rest of the barrel 16, thereby ensuring intimate contact between the inner wall 38 of the barrel 16 and the stopper 412 when the syringe 10 is used. The area 100 may have a depth of about 0.01 mm to about 0.4 mm and desirably a depth of about 0.1 mm to about 0.3 mm.

While this feature of the present invention was discussed in relation to the fifth embodiment, any of the above-described embodiments may include a syringe barrel 16 having such an area 100. Furthermore, if area 100 is not provided, the same stopper design could be made to work by carefully designing the stopper material to undergo only controlled amount of creep (i.e., controlled creep) during the shelf life of the syringe or during its sterilization. In addition, stopper 412 may further include a notch 462 positioned in the lower surface 460 of the flexible roof beneath the tip 434 to tune the stiffness of the flexible roof and/or the main body portion 424 in order to achieve a desired flexing response.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof.

The invention claimed is:

1. A plunger rod and stopper assembly adapted for use with a syringe barrel, the assembly comprising:
   a) a stopper comprising:
      i) a main body portion defining an open rearward end configured to receive the plunger rod, a flange provided along an inner circumference of the main body portion and extending toward a center of the stopper, and a closed front end forming a flexible roof; and
      ii) a first perimetrical skirt extending around an outer circumference of the main body portion toward the closed front end of the main body; and
   b) a plunger rod having a plunger rod body extending along a longitudinal axis, the plunger rod body comprising a front attachment end having a radially extending disk configured to engage the flange of the stopper, the plunger rod including a back end,
   wherein, when fluid pressure is increased inside the syringe barrel during an injection, the flexible roof expands in a radial direction toward an inner wall of the syringe barrel, the first perimetrical skirt is forced against the inner wall of the syringe barrel, and an engagement between the disk and the flange forces the main body portion to expand in the radial direction toward the inner wall of the syringe barrel, thereby providing a sealing pressure between the stopper and the inner wall of the syringe barrel, wherein the disk includes a surface configured to engage a lower surface of the flexible roof to force the main body portion in the radial direction to create a seal between the main body portion and an inner wall of the syringe barrel.

2. The plunger rod and stopper assembly of claim 1, wherein the closed front end of the main body portion includes a first angled portion and a second angled portion, which are both part of the same conical surface that extends to a tip, providing the closed front end with a substantially conical appearance.

3. The plunger rod and stopper assembly of claim 2, wherein the surface of the disk configured to engage the lower surface of the flexible roof is tapered.

4. The plunger rod and stopper assembly of claim 3, wherein the tapered surface is located at a front end of the disk.

5. The plunger rod and stopper assembly of claim 4, wherein the main body portion includes a substantially straight sidewall portion, wherein the first angled portion and the second angled portion extend from a top portion of the straight sidewall portion, and wherein the lower surface of the flexible roof which comes into contact with the tapered surface of the disk is located at the intersection of the first and second angled portion with the sidewall portion of the main body portion.

6. The plunger rod and stopper assembly of claim 1, wherein the flange includes an upwardly angled portion and a downwardly angled portion.

7. The plunger rod and stopper assembly of claim 5, wherein during an aspiration, the downwardly angled portion engages the attachment portion to force the main body portion in a radial direction toward the inner wall of the syringe barrel to create a seal between the main body portion and the inner wall of the syringe barrel.

8. The plunger rod and stopper assembly of claim 1, wherein the engagement between the disk and the flange locks the plunger rod in place and prevents separation of the plunger rod from the stopper.

9. The plunger rod and stopper assembly of claim 1, wherein the plunger rod includes a retaining ring positioned adjacent the open rearward end of the main body portion of the stopper, the retaining ring configured to prevent removal of the plunger rod from the syringe barrel.

10. The plunger rod and stopper assembly of claim 1, wherein the syringe barrel includes an area near a fluid dispensing end having an inner diameter $D_1$ that is greater than an inner diameter $D_2$ of any remaining areas of the syringe barrel, wherein the area of the syringe barrel having the $D_1$ inner diameter is configured to receive the first perimetrical skirt when the stopper and plunger rod are in a storage position.

11. The plunger rod and stopper assembly of claim 10, wherein the area has a depth of about 0.01 mm to about 0.4 mm.

12. The plunger rod and stopper assembly of claim 1, wherein the stopper includes a notch positioned in a lower surface of the closed front end of the main body portion to achieve a desired flexing response of the closed front end of the stopper.

13. A syringe comprising:
   a) a substantially cylindrical syringe barrel comprising a fluid dispensing end and an open end, the syringe barrel including an area near a fluid dispensing end having an inner diameter $D_1$ that is greater than an inner diameter $D_2$ of the remaining area of the syringe barrel;
   b) a stopper configured to be received within the open end of the syringe barrel, the stopper comprising:
      i) a main body portion defining an open rearward end configured to receive a plunger rod, an engagement portion provided along an inner circumference of the main body portion, and a closed front end forming a flexible roof, said flexible roof cooperating with the plunger rod to define a substantially hollow main body portion; and
      ii) a first perimetrical skirt extending around an outer circumference of the main body portion toward the closed front end of the main body portion; and
   c) a plunger rod having a plunger rod body extending along a longitudinal axis, the plunger rod body comprising a front attachment end configured to engage the engagement portion provided along the inner circumference of the main body portion of the stopper,
   wherein the area of the syringe barrel having the $D_1$ inner diameter is configured to receive the first perimetrical skirt when the stopper and plunger rod are in a storage position.

14. The syringe of claim 13, wherein the area has a depth of about 0.01 mm to about 0.4 mm.

15. The syringe of claim 13, wherein the stopper includes a notch positioned in a lower surface of the closed front end of the main body portion to achieve a desired flexing response of the closed front end of the stopper.

16. The syringe of claim 13, wherein, when fluid pressure is increased inside the syringe barrel during an injection, the flexible roof expands in a radial direction toward an inner wall of the syringe barrel, the first perimetrical skirt is forced against the inner wall of the syringe barrel, and an engagement between the plunger rod and the engagement portion forces the main body portion to expand in the radial direction toward the inner wall of the syringe barrel, thereby providing a sealing pressure between the stopper and the inner wall of the syringe barrel.

17. The syringe of claim 16, wherein the engagement portion comprises a flange provided along an inner circumference of the main body portion and extending toward a center of the stopper and wherein the front attachment end of the stopper comprises a radially extending disk having a tapered surface configured to a lower surface of the flexible roof.

18. The syringe of claim 17, wherein the main body portion of the stopper includes a substantially straight sidewall portion, a first angled portion and a second angled portion extending from a top portion of the straight sidewall portion to form the closed front end of the stopper, and wherein the lower surface of the flexible roof that comes into contact with the tapered surface of the disk is located at the intersection of the first and second angled portion with the sidewall portion of the main body portion.

* * * * *